United States Patent
Abbot et al.

(10) Patent No.: US 10,041,043 B2
(45) Date of Patent: Aug. 7, 2018

(54) METHOD OF PRODUCING ERYTHROCYTES WITHOUT FEEDER CELLS

(71) Applicant: Celularity, Inc., Warren, NJ (US)

(72) Inventors: Stewart Abbot, Warren, NJ (US); Lin Kang, Edison, NJ (US); Vanessa Voskinarian-Berse, Millington, NJ (US); Xiaokui Zhang, Livingston, NJ (US)

(73) Assignee: CELULARITY, INC., Warren, NJ (US)

(*) Notice: Subject to any disclaimer, the term of this patent is extended or adjusted under 35 U.S.C. 154(b) by 0 days.

(21) Appl. No.: 14/979,327

(22) Filed: Dec. 22, 2015

(65) Prior Publication Data
US 2016/0362659 A1  Dec. 15, 2016

Related U.S. Application Data

(62) Division of application No. 14/052,524, filed on Oct. 11, 2013, now Pat. No. 9,255,248, which is a division
(Continued)

(51) Int. Cl.
*C12N 5/00* (2006.01)
*C12N 5/02* (2006.01)
(Continued)

(52) U.S. Cl.
CPC ......... *C12N 5/0641* (2013.01); *C12N 5/0018* (2013.01); *C12N 2500/36* (2013.01); *C12N 2500/90* (2013.01); *C12N 2501/105* (2013.01); *C12N 2501/125* (2013.01); *C12N 2501/14* (2013.01); *C12N 2501/145* (2013.01);
(Continued)

(58) Field of Classification Search
CPC ................ C12N 5/0641; C12N 5/0018; C12N 2500/36; C12N 2500/90; C12N 2501/105; C12N 2501/125; C12N 2501/14; C12N 2501/145; C12N 2501/2303; C12N 2501/2311; C12N 2501/26; C12N 2501/90; C12N 2501/998; C12N 2501/999; C12N 2506/03
See application file for complete search history.

(56) References Cited

FOREIGN PATENT DOCUMENTS

WO    WO 99/67360    * 12/1999    ............... C12N 5/00

OTHER PUBLICATIONS

Leberbauer et al., Different steroids co-regulate long-term expansion versus terminal differentiation in primary human erythroid progenitors, Blood, Jan. 1, 2005, vol. 105, No. 1.*
(Continued)

*Primary Examiner* — Reza Ghafoorian
(74) *Attorney, Agent, or Firm* — Celularity, Inc.; Timothy L. Smith; Geoffry T. Knudsen

(57) ABSTRACT

Provided herein are methods of producing erythrocytes from hematopoietic cells, particularly hematopoietic cells from placental perforate in combination with hematopoietic cells from umbilical cord blood, wherein the method results in accelerated expansion and differentiation of the hematopoietic cells to more efficiently produce administrate erythrocytes. Further provided herein is a bioreactor in which hematopoietic cell expansion and differentiation takes place.

10 Claims, 18 Drawing Sheets

Figure 1:
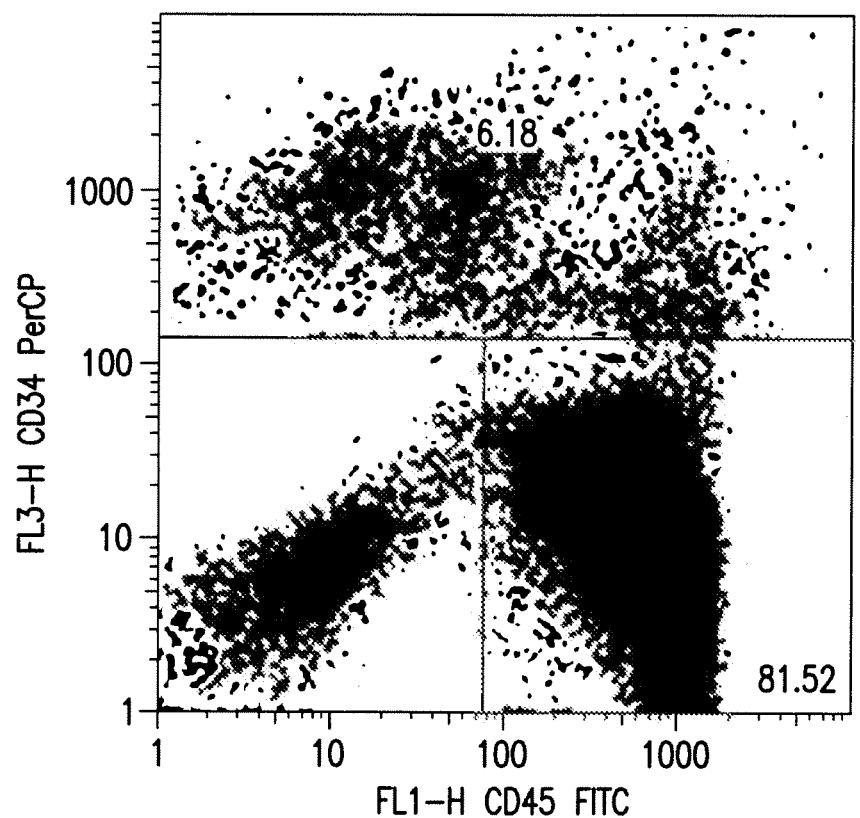

Related U.S. Application Data of application No. 12/829,326, filed on Jul. 1, 2010, now Pat. No. 8,586,360.

(60) Provisional application No. 61/222,930, filed on Jul. 2, 2009.

(51) Int. Cl.
*C12C 1/00* (2006.01)
*C12N 5/078* (2010.01)

(52) U.S. Cl.
CPC ............... *C12N 2501/2303* (2013.01); *C12N 2501/2311* (2013.01); *C12N 2501/26* (2013.01); *C12N 2501/90* (2013.01); *C12N 2501/998* (2013.01); *C12N 2501/999* (2013.01); *C12N 2506/03* (2013.01)

(56) References Cited

OTHER PUBLICATIONS

Verhelle et al., Lenalidomide and CC-4047 Inhibit the Proliferation of Malignant B Cells while Expanding Normal CD34+ Progenitor Cells, Cancer Res 2007; 67: (2). Jan. 15, 2007.*

* cited by examiner

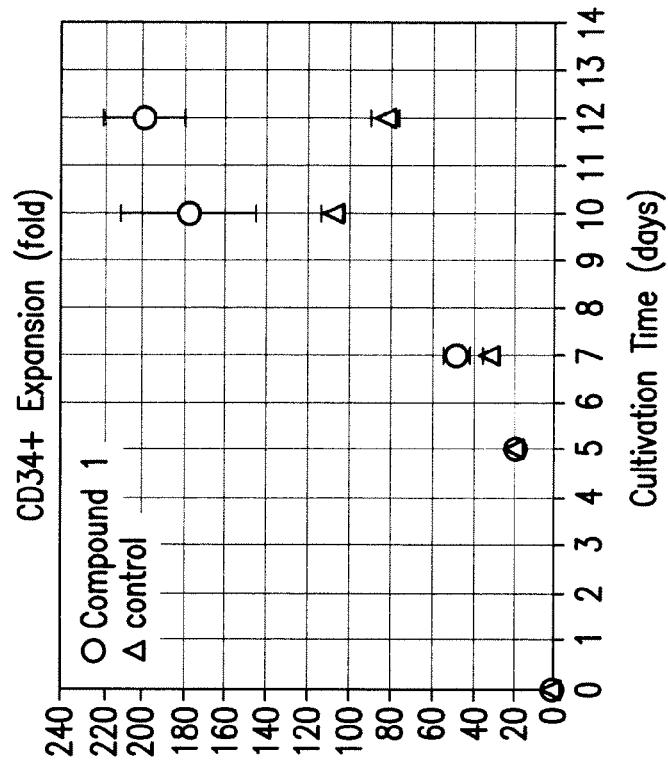
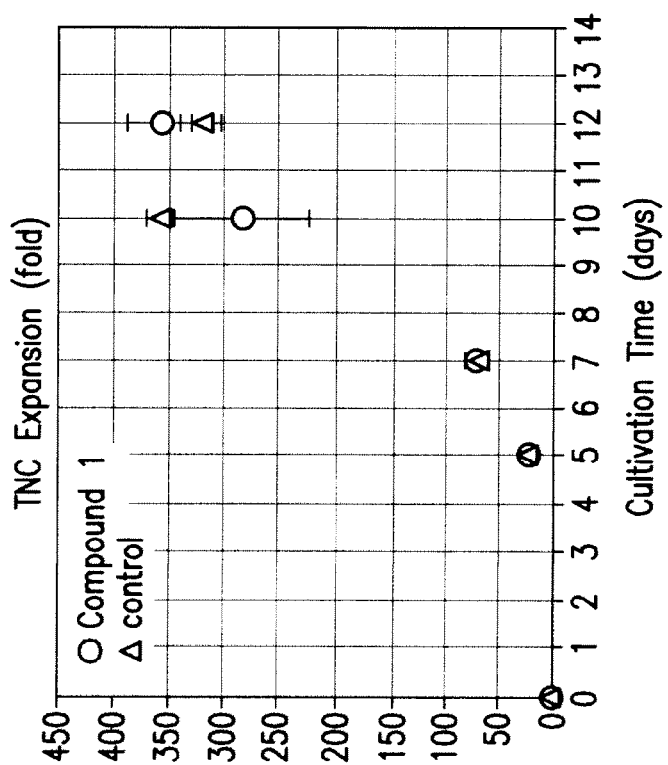
FIG. 3A
FIG. 3B

METHOD OF PRODUCING ERYTHROCYTES WITHOUT FEEDER CELLS This application is a divisional of U.S. application Ser. No. 14/052,524, filed Oct. 11, 2013, which is a divisional of U.S. application Ser. No. 12/829,326, filed Jul. 1, 2010, now U.S. Pat. No. 8,586,360, which claims benefit of U.S. Provisional Application No. 61/222,930, filed Jul. 2, 2009, each of which is incorporated by reference herein in its entirety.

1. FIELD

Provided herein, generally, are methods of expanding hematopoietic cell populations, e.g., CD34+ cell populations, and methods of producing administrate units of erythrocytes from such cell populations. Also provided herein is a bioreactor that accomplishes such expansion and differentiation.

2. BACKGROUND

Each year in the United States approximately 13 million units of blood are used for transfusion or to generate life-saving blood products such as platelets. Voluntary blood donation is utilized by the Red Cross and other agencies to procure from about 500 mL to about 1000 mL whole blood samples. Self-screening of voluntary donation is relatively safe and effective in the US and Western Europe where the incidences of HIV and other adventitious pathogens are relatively low. However, to countries in which HIV and hepatitis are endemic, procurement of safe blood for transfusion can be highly problematic. As an alternative to voluntary blood donation many groups have attempted to develop safe artificial blood substitutes that could undergo long-term storage. While some of these products show significant promise in transiently treating traumatic blood loss, such products are not designed for long-term substitution of red blood cell function. Increasingly there is a need to develop a safe and plentiful supply of erythrocytes that can be administered to patients on the battlefield or civilian hospital settings around the world.

Conventional methods for producing erythrocytes are either inefficient, too small in scale, or too laborious to allow for the continuous, on-site production of erythrocytes. Conventional dish or flask-based culture systems are associated with discontinuous medium exchange, and generally dish-based culture systems cannot be used to handle single batches of >$10^9$ cells. A logical further development from dishes are bag technologies, e.g. the Wave Bioreactor, in which the medium volume is significantly enlarged by using bags and cell attachment surface can be enlarged by using buoyant carriers. However, bag-type reactors typically operate from $2\times10^6$ to about $6\times10^6$ cells/ml medium, requiring significant media dilution during culture and a laborious 10-100 fold debulking. Moreover, bag technologies, and generally all large-vessel stirred tank type bioreactors, do not provide tissue-like physiologic environments that are conducive to "normal" cell expansion and differentiation.

3. SUMMARY

Provided herein are methods of expanding hematopoietic cells (e.g., hematopoietic stem cells or hematopoietic progenitor cells), to differentiating the expanded hematopoietic cells into administrate erythrocytes (red blood cells), and to the production of administrable units of cells comprising the erythrocytes.

In one aspect, provided herein is a method of producing erythrocytes. In one embodiment, the method comprises differentiating hematopoietic cells from human placental perfusate to erythrocytes, wherein the method comprises expanding a population of hematopoietic cells in the absence of a feeder layer; and differentiating the hematopoietic cells to erythrocytes or progenitors of erythrocytes.

In another aspect, provided herein is a bioreactor for the expansion of hematopoietic cells and differentiation of said hematopoietic cells into erythrocytes. The bioreactor allows for production of a number of erythrocytes equivalent to current methods of producing erythrocytes, in a much smaller volume, by facilitating a continuous erythrocyte production method rather than a batch method. In specific embodiments, the bioreactor comprises a cell culture element, a cell separation element, a gas provision element and/or a medium provision element. In a specific embodiment of the bioreactor, the erythrocytes are collected by magnetic bead separation. In another embodiment of the method, the erythrocytes are collected by partially or fully deoxygenating hemoglobin in said erythrocytes, and attracting the erythrocytes to a surface using a magnetic field.

In another aspect, provided herein is a method of the production of erythrocytes using the bioreactor described herein. In a specific embodiment, provided herein is a method of producing erythrocytes comprising producing erythrocytes using a plurality of the bioreactors disclosed herein. In other specific embodiments of the method, the production of said erythrocytes is automated.

In one aspect, provided herein is a method of producing erythrocytes, comprising expanding a population of hematopoietic cells in a medium in the absence of feeder cells, wherein a plurality of hematopoietic cells within said population of hematopoietic cells differentiate into erythrocytes during said expanding; and isolating said erythrocytes from said medium, wherein said medium comprises SCF at a concentration of about 10 to about 10,000 ng/mL, IL-3 at a concentration of about 0.01 to about 500 ng/mL and EPO at a concentration of about 0.1 to about 10 IU/mL, and wherein said SCF, IL-3 and Epo are not comprised within an undefined component of said medium (e.g., serum). In a specific embodiment of the method, said medium does not comprise one or more, or any, of Flt-3L, IL-11, thrombopoietin (Tpo), homeobox-B4 (HoxB4), or methylcellulose. In other specific embodiments, said medium comprises SCF at a concentration of about 20 to about 2000 ng/mL; about 50 to about 1000 ng/mL; or about 100 ng/mL. In other specific embodiments, said medium comprises IL-3 at a concentration of about 0.1 to about 100 ng/mL; about 1 to about 50 ng/mL; or about 5 ng/mL. In other specific embodiments, said medium comprises EPO at a concentration of about 1 to about 5 IU/mL; or about 2 to about 3 IU/mL.

In another specific embodiment of the method, said medium further comprises insulin-like growth factor 1 (IGF-1) at a concentration of about 1 to about 1000 ng/mL and lipids at a concentration of about 1 to about 1000 μg/mL, wherein said lipids comprise a mixture of protein and cholesterol; and wherein said medium comprises hydrocortisone at a concentration of about 0.01 to about 100 μM, or dexamethasone at a concentration of about 0.01 μM to about 100 μM. In more specific embodiments, said medium comprises IGF-1 at a concentration of about 10 to about 500 ng/mL; or about 20 to about 100 ng/mL. In other more specific embodiments, said medium comprises lipids at a concentration of about 10 to about 500 ng/mL; or about 20 to about 100 ng/mL. In other more specific embodiments, said medium comprises hydrocortisone at a concentration of about 0.1 to about 50 µM; or about 0.5 to about 10 µM. In other more specific embodiments, said medium comprises dexamethasone at a concentration of about 0.05 to about 20 µM; or about 0.1 to about 10 µM.

In a more specific embodiment, the medium comprises about 100 ng/mL SCF, about 3 U/mL Epo, about 40 ng/mL IGF-1, about 5 ng/mL IL-3, about 1 µM Dexamethasone. and 40 µg/ml lipids, wherein said lipids comprise a mixture of protein and cholesterol. In another more specific embodiment, the medium comprises about 100 ng/mL SCF, about 2 U/mL Epo, about 40 ng/mL IGF-1, about 5 ng/mL IL-3, about 1 µM hydrocortisone, and 50 ng/ml lipids, wherein said lipids comprise a mixture of protein and cholesterol.

In certain other embodiments, hematopoietic cells, in certain embodiments, are expanded and differentiated, in continuous fashion, in a culture medium comprising SCF; Epo; IGF-1; lipids, wherein the lipids comprise a mixture of proteins and cholesterol (e.g., Lipids Cholesterol Rich from adult bovine serum; Cat. No. C7305-1G, Sigma, St Louis, Mo.); and either hydrocortisone or dexamethasone. In specific embodiments, said medium comprises SCF at a concentration of about 10 to about 10,000 ng/mL; about 20 to about 2000 ng/mL; about 50 to about 1000 ng/mL; about 100 ng/mL; or about 100 ng/mL. In other specific embodiments, said medium comprises Epo at a concentration of about 1 to about 5 IU/mL; or about 2 to about 3 IU/mL. In other specific embodiments, said medium comprises IGF-1 at a concentration of about 1 to about 1000 ng/mL; about 10 to about 500 ng/mL; about 20 to about 100 ng/mL; or about 40 ng/mL. In other specific embodiments, said medium comprises said lipids at a concentration of about 1 to about 1000 µg/mL; about 10 to about 500 ng/mL; about 20 to about 100 ng/mL; or about 40 ng/mL. In other specific embodiments, said medium comprises hydrocortisone at a concentration of about 0.1 µM to about 10 µM; about 0.5 µM to about 5 µM; or about 1 µM. In other specific embodiments, said medium comprises dexamethasone at a concentration of about 0.1 µM to about 10 µM; about 0.5 µM to about 5 µM; or about 1 µM.

In another specific embodiment of the method, the medium comprises an immunomodulatory compound, wherein the immunomodulatory compound increases the number of hematopoietic cells compared to a plurality of hematopoietic cells expanded in the absence of the immunomodulatory compound.

In a specific embodiment of any of the above media, the medium is serum-free.

In another specific embodiment of the method, said hematopoietic cells are $CD34^+$. In another specific embodiment, said hematopoietic cells are $Thy-1^+$, $CXCR4^+$, $CD133^+$ or $KDR^+$. In another specific embodiment, said hematopoietic cells are $CD34^-D133^+$ or $CD34^-CD117^+$. In another specific embodiment, said hematopoietic cells are $CD45^-$. In another specific embodiment, hematopoietic cells are $CD2^-$, $CD3^-$, $CD11b^-$, $CD11c^-$, $CD14^-$, $CD-16^-$, $CD19^+$, $CD24^-$, $CD56^-$, $CD66b^-$ and/or glycophorin $A^-$.

In another specific embodiment, said hematopoietic cells are obtained from cord blood, placental blood, peripheral blood, bone marrow, embryonic stem cells or induced pluripotent cells. In another specific embodiment, said hematopoietic cells are obtained from placental perfusate. In another specific embodiment, said hematopoietic cells are obtained from umbilical cord blood and placental perfusate. In a more specific embodiment, said placental perfusate is obtained by passage of perfusion solution through only the vasculature of a placenta. In another specific embodiment, said hematopoietic cells are human hematopoietic cells.

In certain embodiments of the method, a plurality of said hematopoietic cells is blood type A, blood type O, blood type AB, blood type O; is Rh positive or Rh negative; blood type M, blood type N, blood type S, or blood type s; blood type P1; blood type Lua, blood type Lub, or blood type Lu(a); blood type K (Kell), k (cellano), Kpa, Kpb, K(a+), Kp(a−b−) or K− K− Kp(a−b−); blood type Le(a−b−), Le(a+b−) or Le(a−b+); blood type Fy a, Fy b or Fy(a−b−); or blood type Jk(a−b−), Jk(a−b−), Jk(a−b+) or Jk(a+b+). In a more specific embodiment, the hematopoietic cells are type O, Rh positive; type O, Rh negative; type A, Rh positive; type A, Rh negative; type B, Rh positive; type B, Rh negative; type AB, Rh positive or type AB, Rh negative. In other specific embodiments of the method, greater than 90%, 95%, 98%, or 99%, or each, of said hematopoietic cells is blood type A, blood type O, blood type AB, blood type O; is Rh positive or Rh negative; blood type M, blood type N, blood type S, or blood type s; blood type P1; blood type Lua, blood type Lub, or blood type Lu(a); blood type K (Kell), k (cellano), Kpa, Kpb, K(a+), Kp(a−b−) or K− k− Kp(a−b−); blood type Le(a−b−), Le(a+b−) or Le(a−b+); blood type Fy a, Fy b or Fy(a−b−); or blood type Jk(a−b−), Jk(a+b−), Jk(a−b+) or Jk(a+b+). In more specific embodiments, the hematopoietic cells are type O, Rh+; type O, Rh negative; type A, Rh positive; type A, Rh negative; type B, Rh positive; type B, Rh negative; type AB, Rh positive or type AB, Rh negative.

Further provided herein are compositions, e.g., compositions comprising erythrocytes, made by any of the methods described above. In a specific embodiment of the compositions, the percentage of cells in said composition having fetal hemoglobin relative to the total number of cells having hemoglobin is about 70 to about 99%. In another specific embodiment, the percentage of cells having adult hemoglobin relative to the total number of cells having hemoglobin is about 5 to about 40%.

In certain embodiments, isolation of erythrocytes from medium in which the erythrocytes differentiate is performed continuously. In other specific embodiments, isolation of erythrocytes is performed periodically, e.g., every 1, 2, 3, 4, 5, 6, 7, 8, 9, 10, 15, 20, 25, 30, 35, 40, 45, 50, 55 or 60 minutes, or every 1, 1.5, 2, 2.5, 3, 3.5, 4, 4.5, 5, 5.5, 6, 6.5, 7.0, 7.5, 8.0, 8.5, 9.0, 9.5, 10.0, 10.5, 11.0, 11.5, 12, 13, 14, 15, 16, 17, 18, 19, 20, 21, 22, 23 or 24 hours, or more during expansion and differentiation of the hematopoietic cells. In another specific embodiment, said isolation of erythrocytes is performed periodically when one or more culture condition criteria are met. e.g., achievement in the culture of a particular cell density; achievement in the culture of a particular number of cells per milliliter expressing certain erythrocyte markers, e.g., CD36 or glycophorin A; or the like.

In another aspect, provided herein is medium for growth or differentiation of hematopoietic cells, wherein said medium comprises stem cell factor SCF at a concentration of about 10 to about 10,000 ng/mL, IL-3 at a concentration of about 0.01 to about 500 ng/mL, and EPO at a concentration of about 0.1 to about 101 U/mL, and wherein said SCF, IL-3 and Epo are not comprised within an undefined component of said medium (e.g., scrum). In a specific embodiment, said medium does not comprise one or more, or any, of Flt-3L, IL-11, thrombopoietin (Tpo), homeobox-B4 (HoxB4), or methylcellulose. In other specific embodiments, said medium comprises SCF at a concentration of about 20 to about 2000 ng/mL; about 50 to about 1000 ng/mL; or about 100 ng/mL. In other specific embodiments, said medium comprises IL-3 at a concentration of about 0.1 to about 100 ng/mL; about 1 to about 50 ng/mL; or about 5 ng/mL. In other specific embodiments, said medium comprises EPO at a concentration of about 1 to about 5 IU/mL; or about 2 to about 3 IU/mL.

In another specific embodiment, said medium further comprises insulin-like growth factor 1 (IGF-1) at a concentration of about 1 to about 1000 ng/mL and lipids at a concentration of about 1 to about 1000 μg/mL, wherein said lipids comprise a mixture of protein and cholesterol; and wherein said medium comprises hydrocortisone at a concentration of about 0.01 to about 100 μM, or dexamethasone at a concentration of about 0.01 μM to about 100 μM. In more specific embodiments, said medium comprises IGF-1 at a concentration of about 10 to about 500 ng/mL; or about 20 to about 100 ng/mL. In other more specific embodiments, said medium comprises lipids at a concentration of about 10 to about 500 ng/mL; or about 20 to about 100 ng/mL. In other more specific embodiments, said medium comprises hydrocortisone at a concentration of about 0.1 to about 50 μM; or about 0.5 to about 10 μM. In other more specific embodiments, said medium comprises dexamethasone at a concentration of about 0.05 to about 20 μM; or about 0.1 to about 10 μM.

In a more specific embodiment, the medium comprises about 100 ng/mL SCF, about 3 U/mL Epo, about 40 ng/mL IGF-1, about 5 ng/mL IL-3, about 1 μM Dexamethasone, and 40 μg/ml lipids, wherein said lipids comprise a mixture of protein and cholesterol. In another more specific embodiment, the medium comprises about 100 ng/mL SCF, about 2 U/mL Epo, about 40 ng/mL IGF-1, about 5 ng/mL IL-3, about 1 μM hydrocortisone, and 50 ng/ml lipids, wherein said lipids comprise a mixture of protein and cholesterol.

In another specific embodiment, the medium comprises Iscove's Modified Dulbecco's Medium or RPM1 and is further supplemented with 1% Bovine Serum Albumin; 10 microgram/mL Recombinant Human Insulin; 100 microgram/mL Human Transferrin (Iron saturated); and 0.1 μM 2-Mercaptoethanol; 2 mM L-glutamine.

In certain other embodiments, the medium comprises SCF; Epo; IGF-1; lipids, wherein the lipids comprise a mixture of proteins and cholesterol (e.g., Lipids Cholesterol Rich from adult bovine serum; Cat. No. C7305-1G, Sigma. St Louis, Mo.); and either hydrocortisone or dexamethasone. In specific embodiments, said medium comprises SCF at a concentration of about 10 to about 10,000 ng/mL; about 20 to about 2000 ng/mL; about 50 to about 1000 ng/mL; about 100 ng/mL; or about 100 ng/mL. In other specific embodiments, said medium comprises Epo at a concentration of about 1 to about 5 IU/mL; or about 2 to about 3 IU/mL. In other specific embodiments, said medium comprises IGF-1 at a concentration of about 1 to about 100 ng/mL; about 10 to about 500 ng/mL; about 20 to about 100 ng/mL; or about 40 ng/mL. In other specific embodiments, said medium comprises said lipids at a concentration of about 1 to about 1000 μg/mL; about 10 to about 500 ng/mL; about 20 to about 100 ng/mL; or about 40 ng/mL. In other specific embodiments, said medium comprises hydrocortisone at a concentration of about 0.1 μM to about 10 μM; about 0.5 μM to about 5 μM; or about 1 μM. In other specific embodiments, said medium comprises dexamethasone at a concentration of about 0.1 μM to about 10 μM; about 0.5 μM to about 5 μM; or about 1 μM.

As used herein, the term "hematopoietic cells" includes hematopoietic stem cells and hematopoietic progenitor cells, that is, blood cells able to differentiate into erythrocytes.

As used herein, "+", when used to indicate the presence of a particular cellular marker, means that the cellular marker is detectably present in fluorescence activated cell sorting over an isotype control; or is detectable above background in quantitative or semi-quantitative RT-PCR.

As used herein, "−", when used to indicate the presence of a particular cellular marker, means that the cellular marker is not detectably present in fluorescence activated cell sorting over an isotype control; or is not detectable above background in quantitative or semi-quantitative RT-PCR.

4. BRIEF DESCRIPTION OF THE FIGURES

FIG. 1: Flow cytometric analysis of HPP-derived $CD34^+/CD45^-$ and $CD34^+/CD45^+$ cells.

Figure 2B:
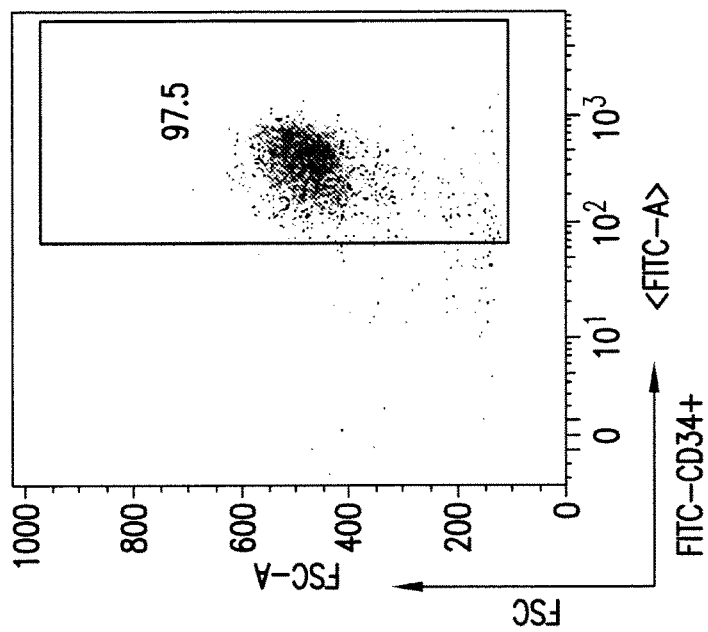
Figure 2A:
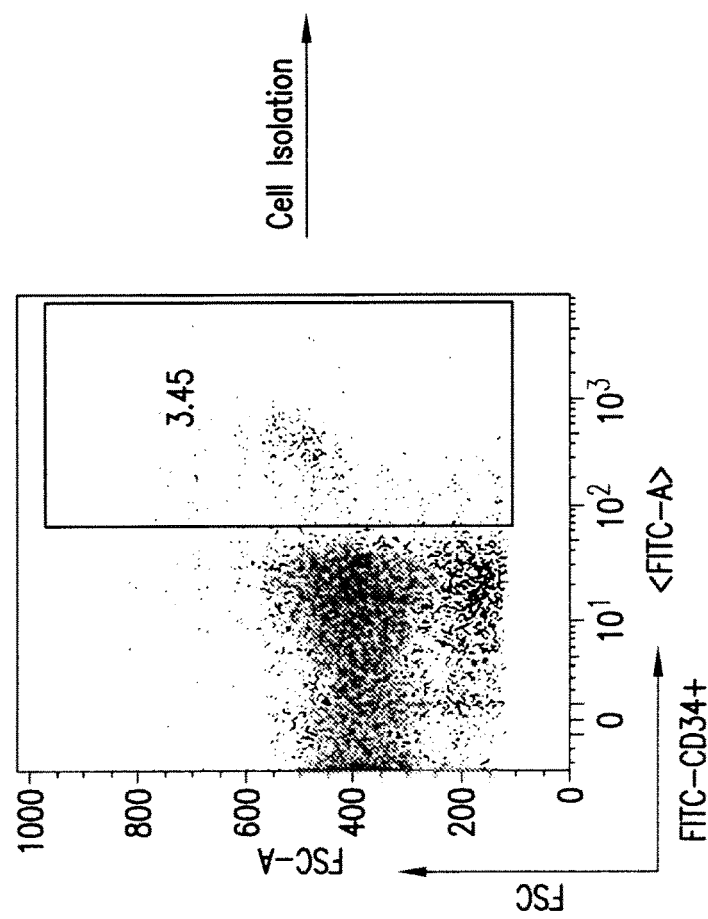

FIGS. 2A, 2B: Flow cytometric analysis of recovered $CD34^+$ cells. (A); $CD34^+$ cells prior to isolation; (B) $CD34^+$ cells after isolation.

FIGS. 3A, 3B: Cell expansion in pomalidomide supplemented IMDM medium. FIG. 3A: Fold expansion of total nucleated cells (TNC). FIG. 3B: Fold expansion of $CD34^+$ cells.

Figure 4A:
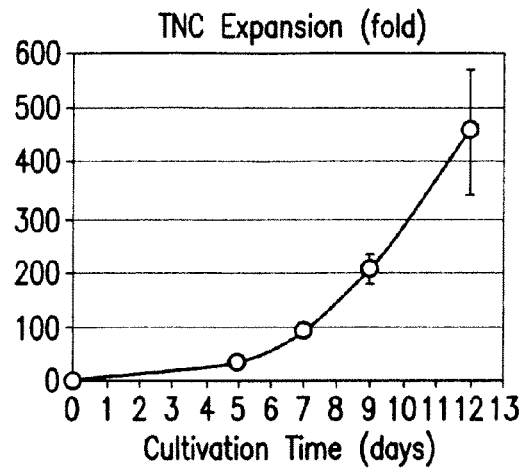
Figure 4B:
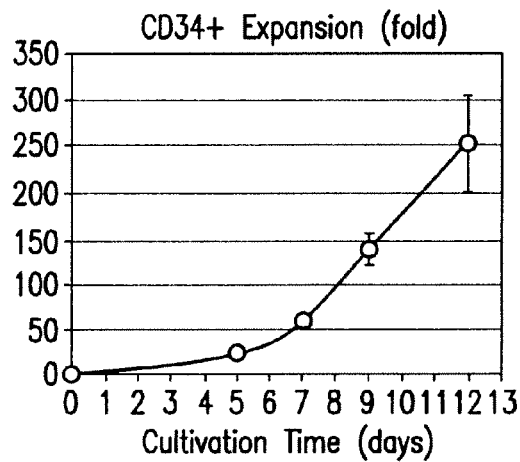
Figure 4C:
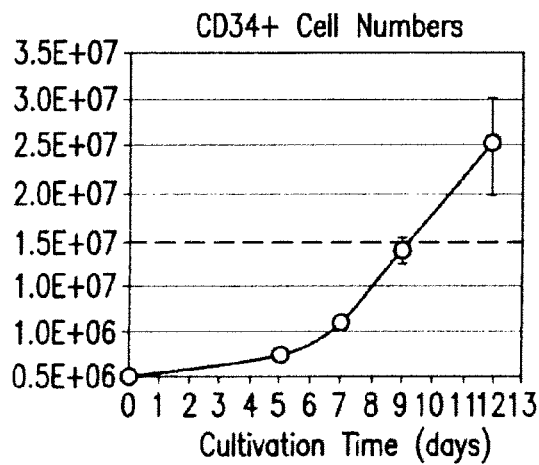

FIGS. 4A-4C: Expandability of $CD34^+$ cultures. FIG. 4A: Fold expansion of TNC. FIG. 4B: Fold expansion of $CD34^+$ cells. FIG. 4C: Expansion of $CD34^+$ cells in number of cells. "Compound 1" is pomalidomide.

Figure 5:
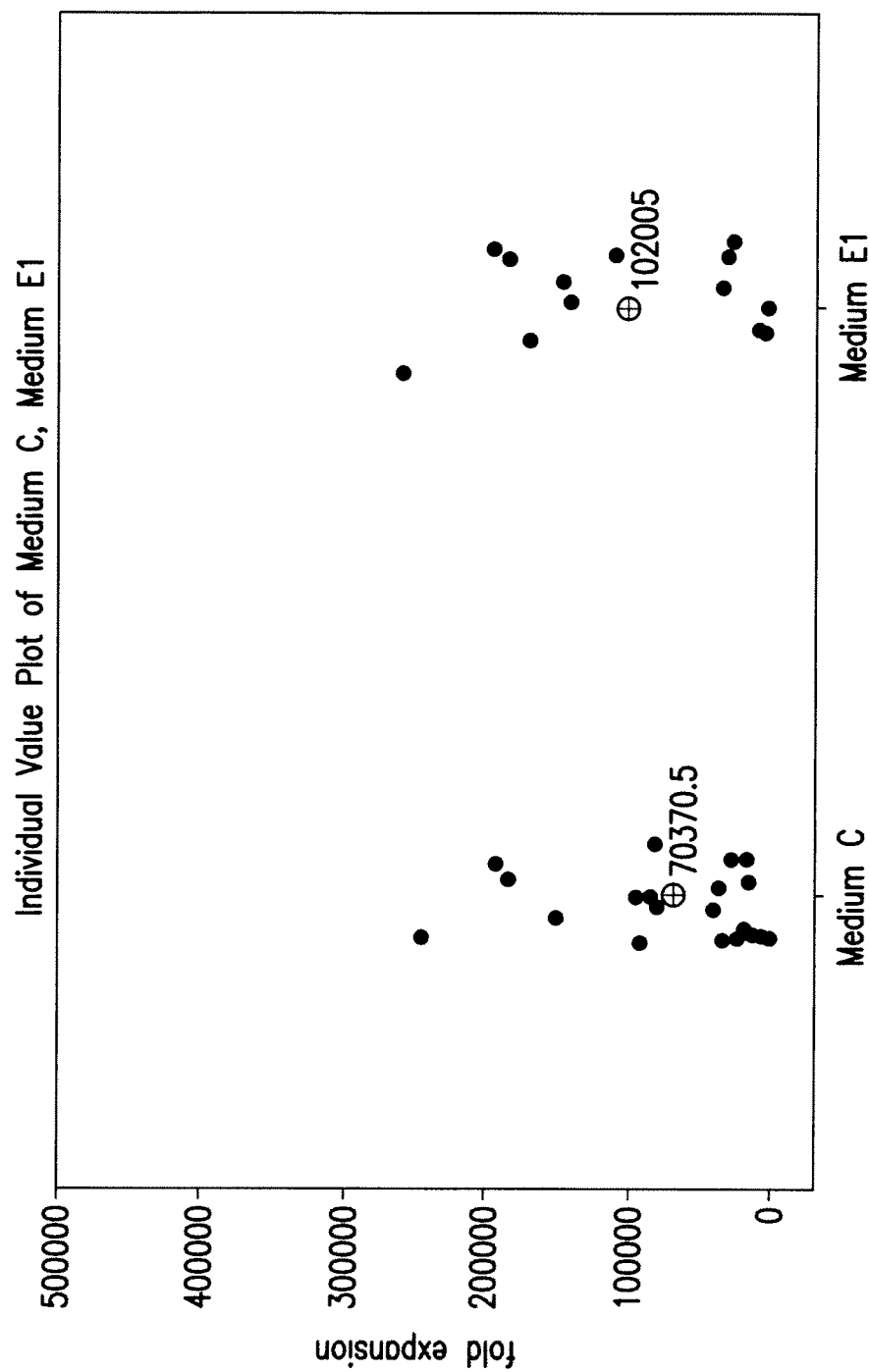

FIG. 5: Cell expansion in medium formulations C and E1.

Figure 6:
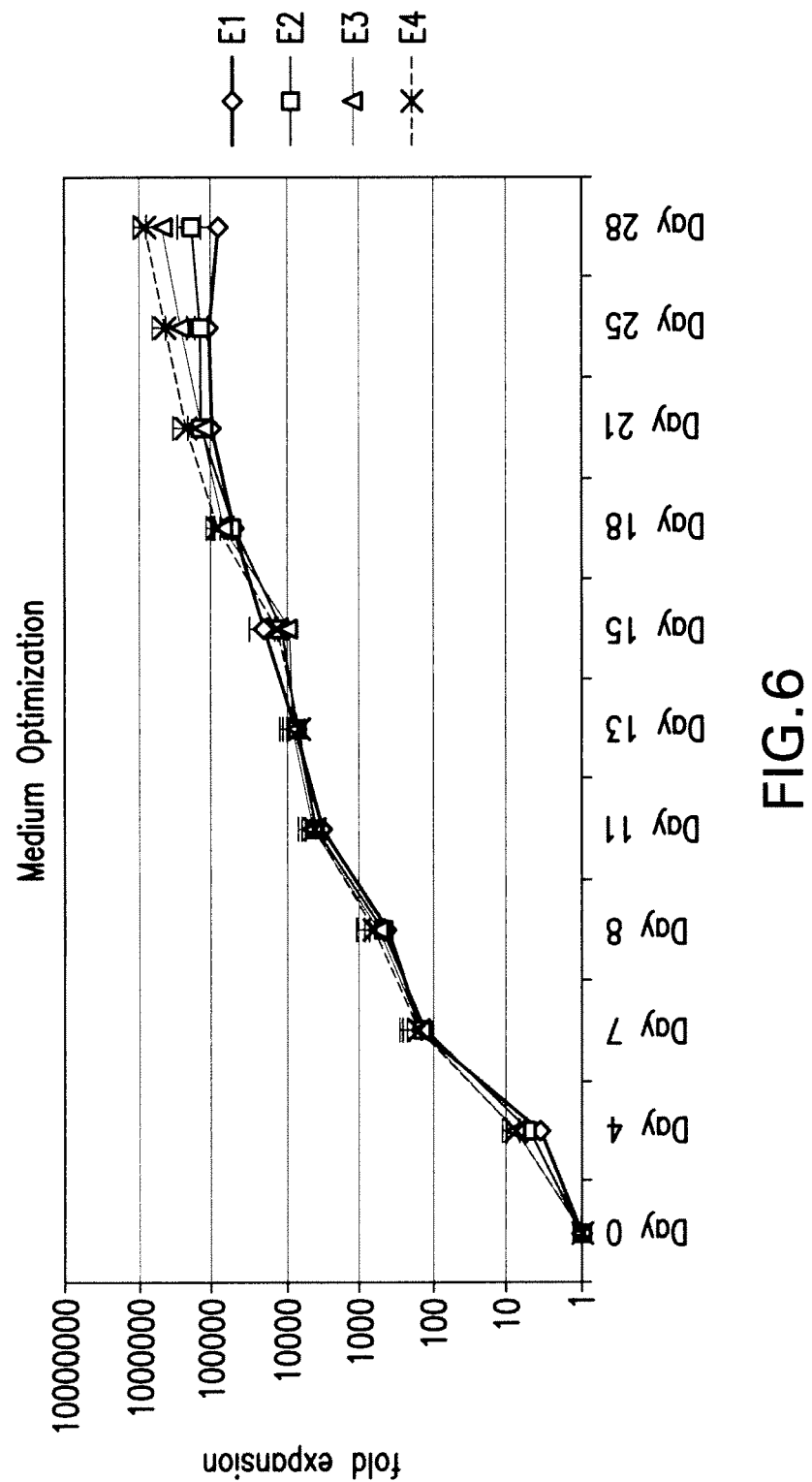

FIG. 6: Medium optimization—E1, E2, E3 and E4. Error bars represent the standard deviation calculated tor population means for 3 donors.

Figure 7:
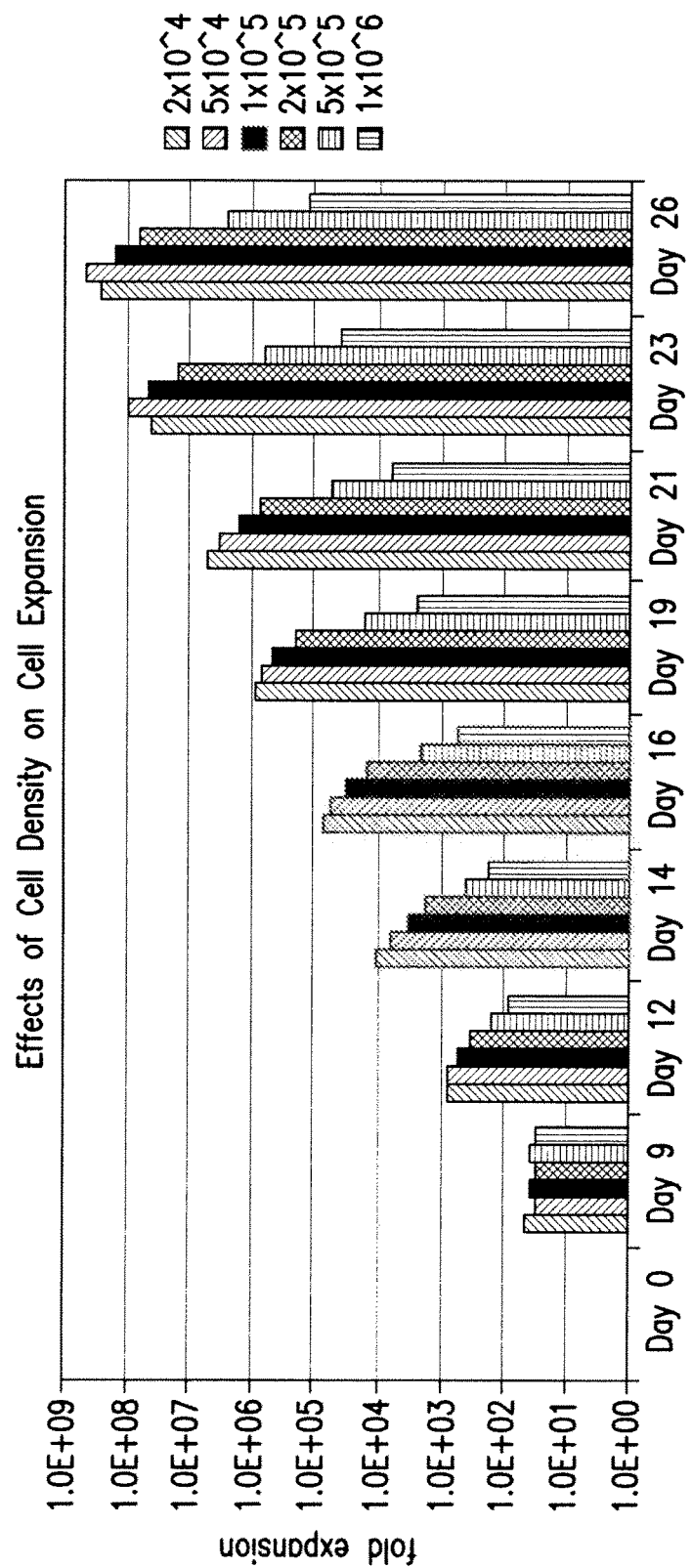

FIG. 7: Effects of cell density on cell expansion.

Figure 8:
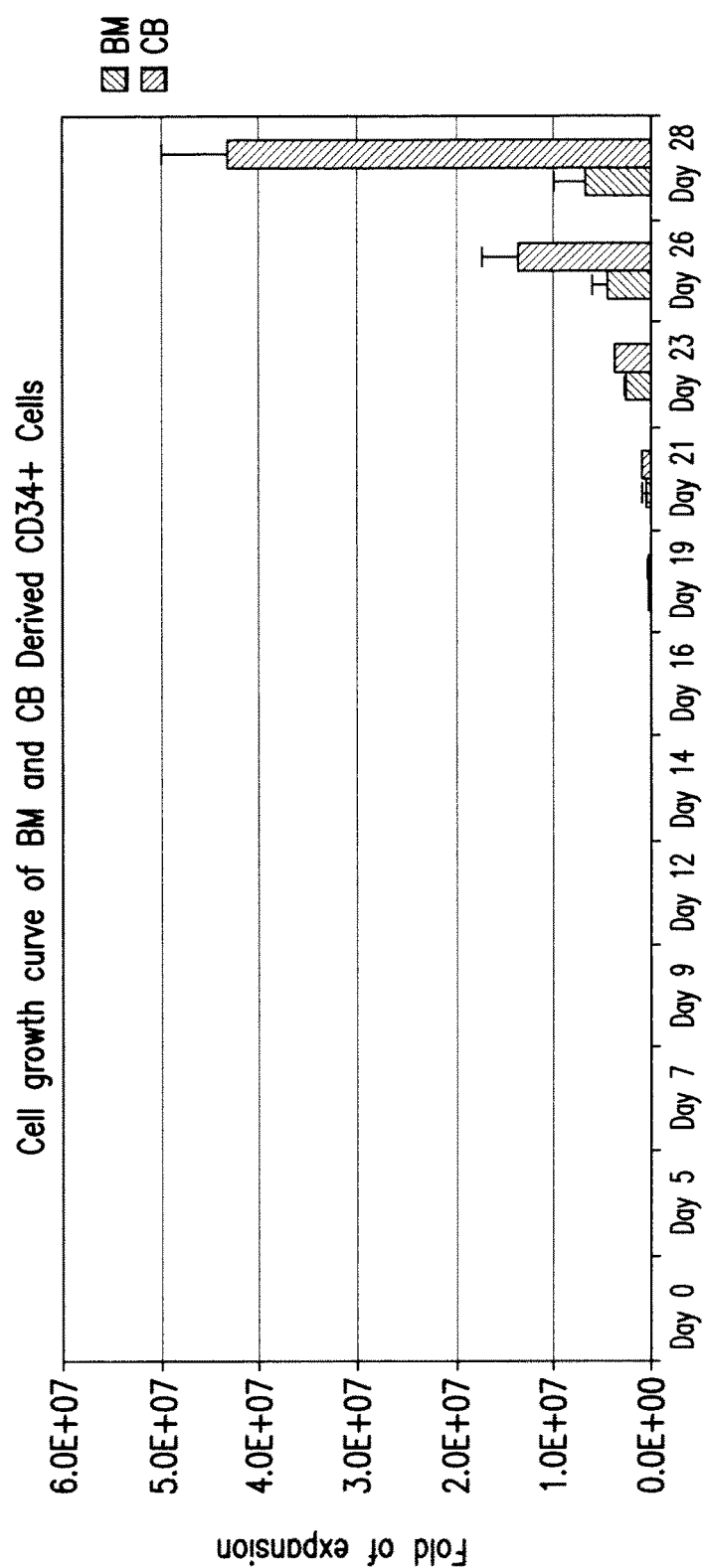

FIG. 8: Comparison of proliferation potential of BM and CB derived CD34+ cells. Standard deviation was calculated for population means for 3 donors.

Figure 9A:
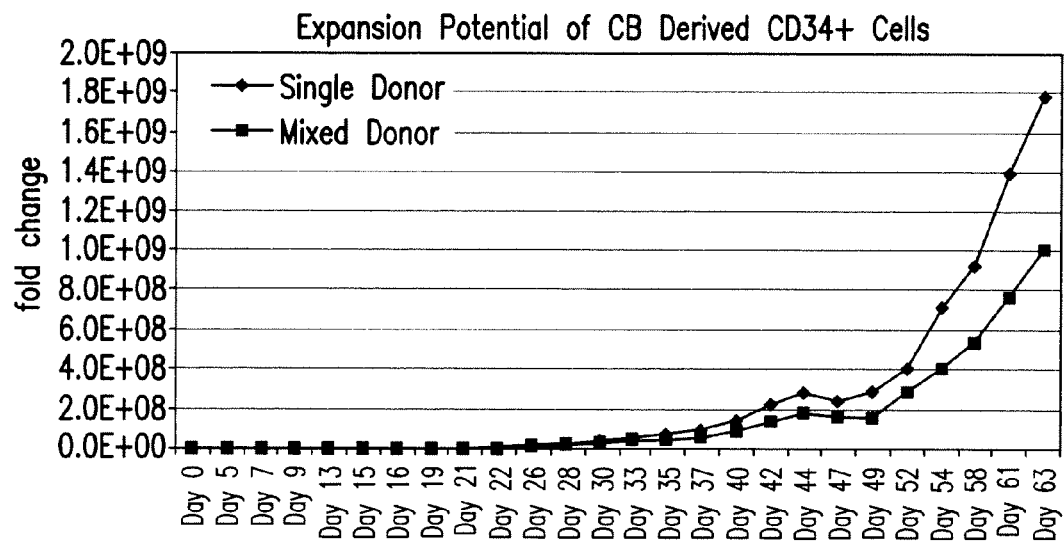
Figure 9B:
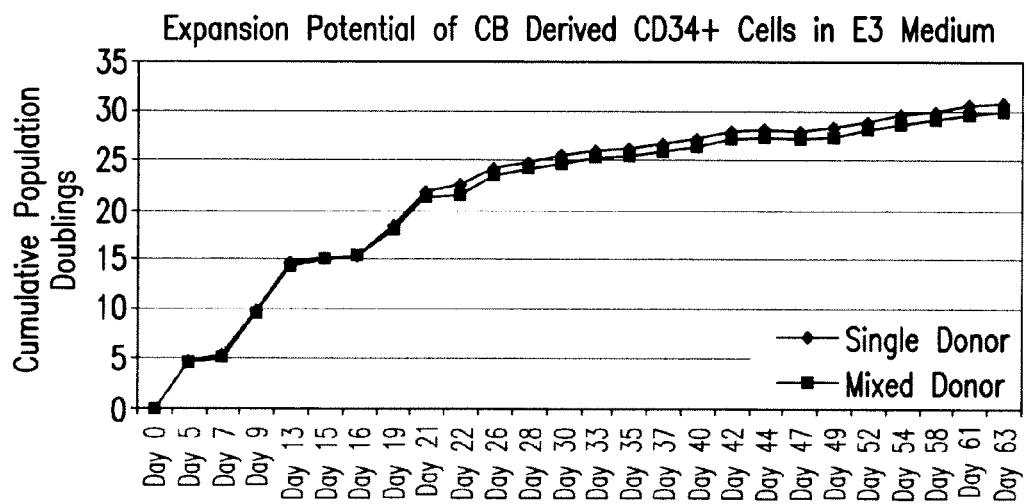

FIGS. 9A, 9B: Long term cultures in E3 medium. (A) Oil fold expansion; (B) Population doublings.

Figure 10A:
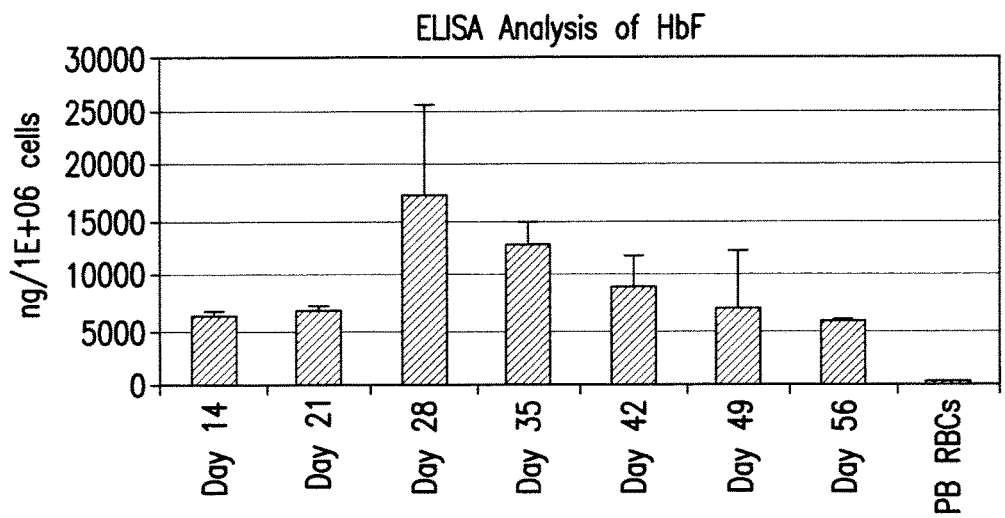
Figure 10B:
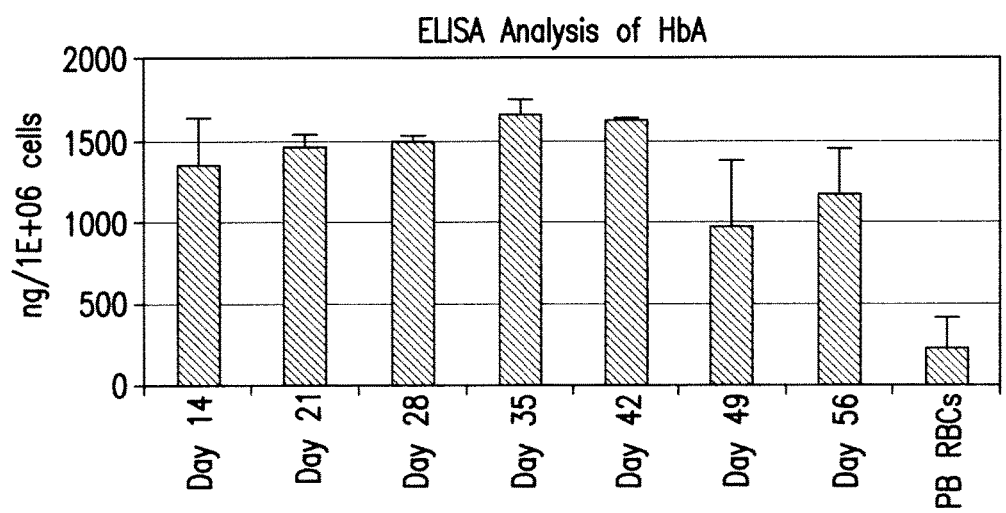

FIGS. 10A, 10B; ELISA analysis of HbF and HbA production. (A) HbF production; (B) HbA production. Standard deviation was calculated for means for 3 replicates.

Figure 11:
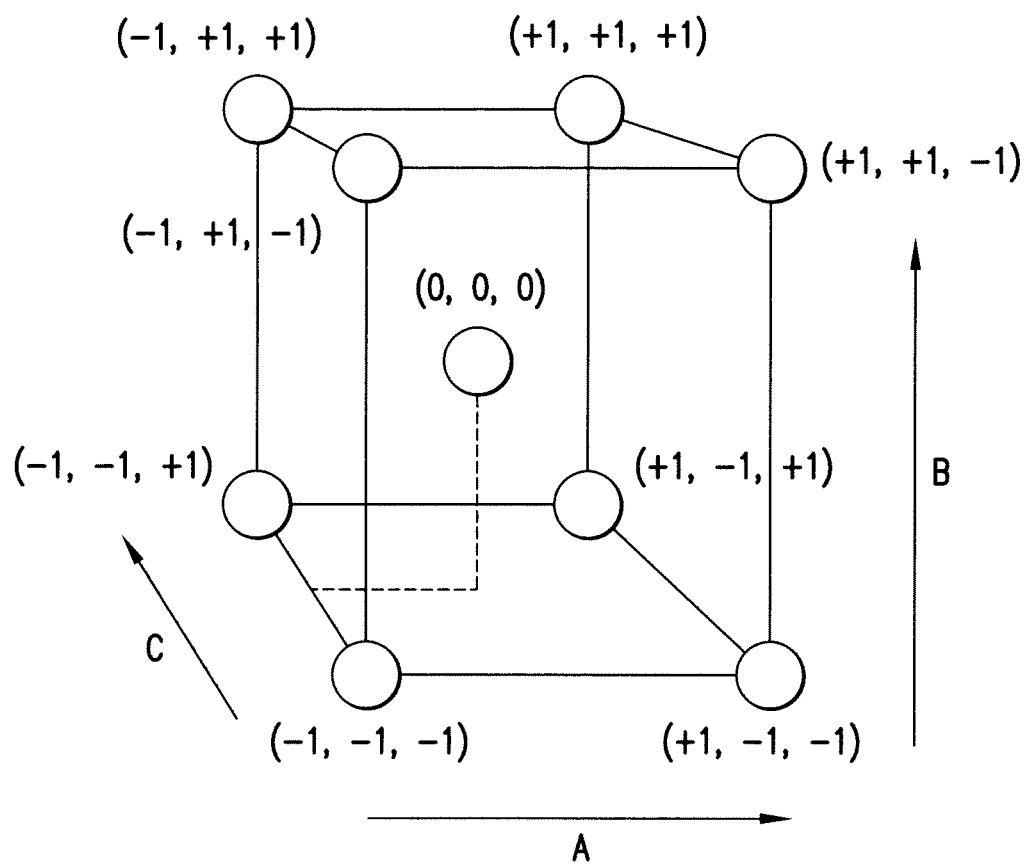

FIG. 11: 3-level design of experiment (DOE) study to delineate interactions among SCF, Epo and IL-3. Full factorial experiment design.

Figure 12A:
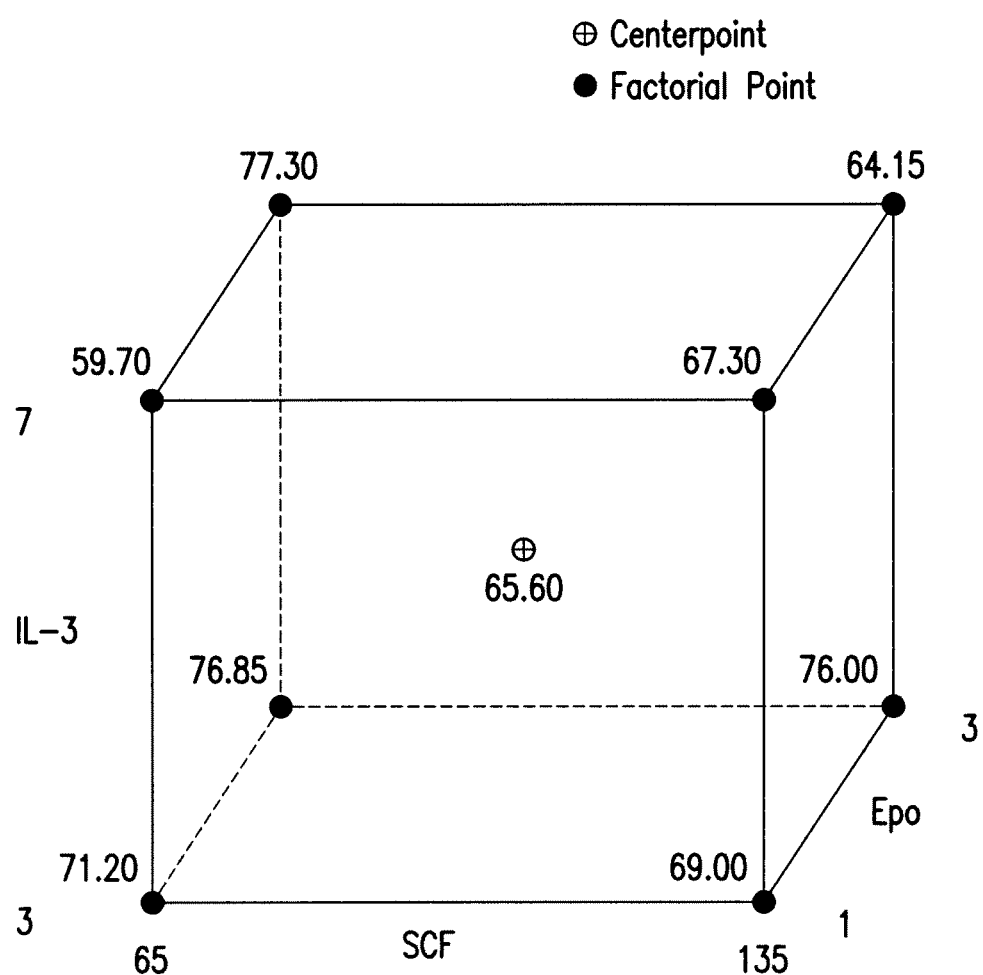
Figure 12B:
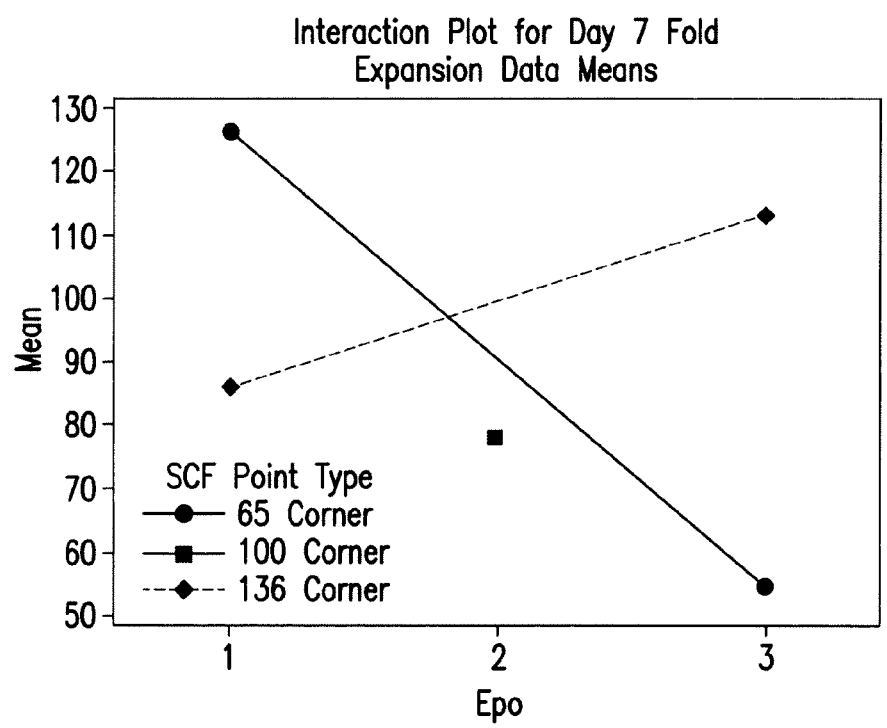
Figure 12C:
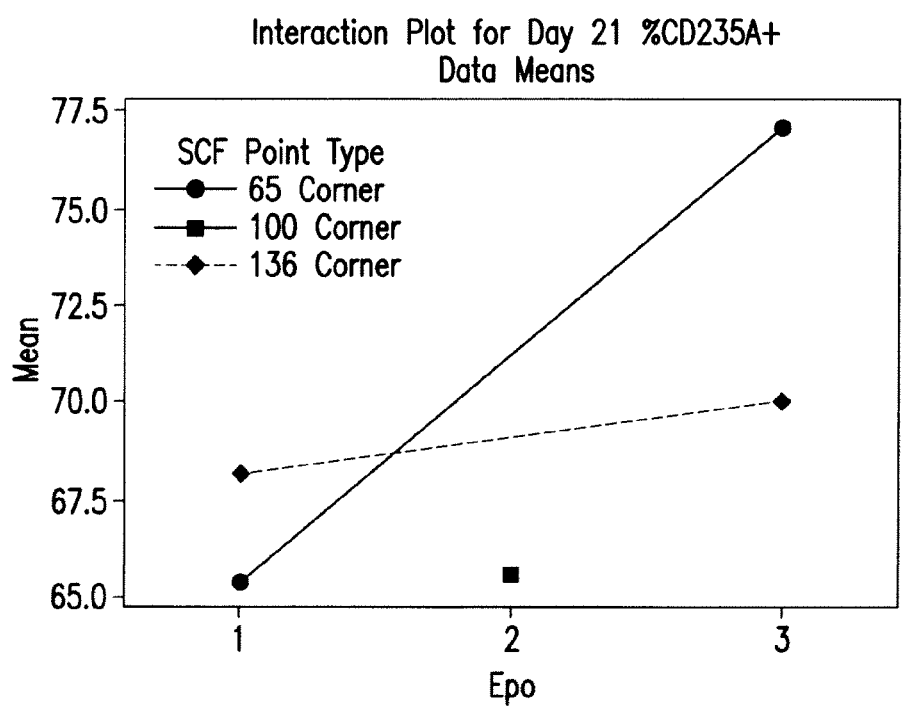

FIGS. 12A-12C: 3-level DOE study to delineate interactions among SCF, Epo and IL-3. Cube plot for factorial effects on cell differentiation (FIG. 12A); interaction plots of SCF (FIG. 12B) and Epo (FIG. 12C) on cell expansion and differentiation.

Figure 13A:
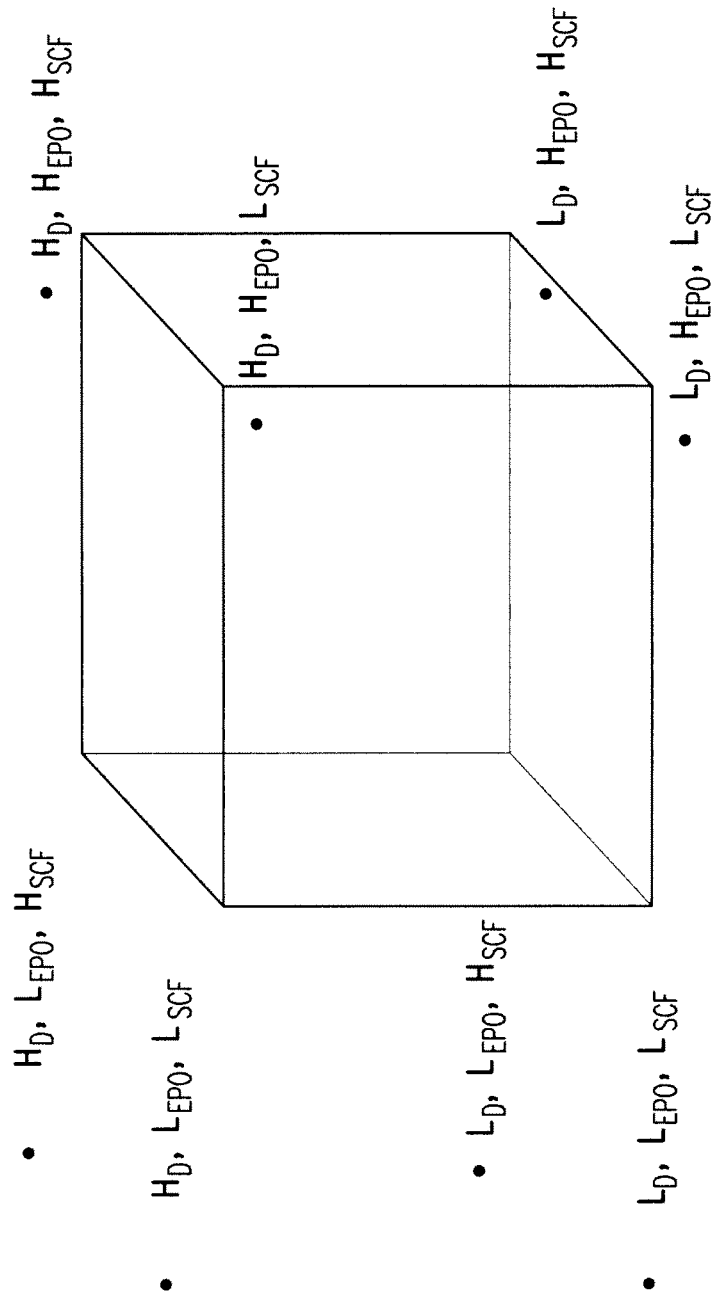
Figure 13B:
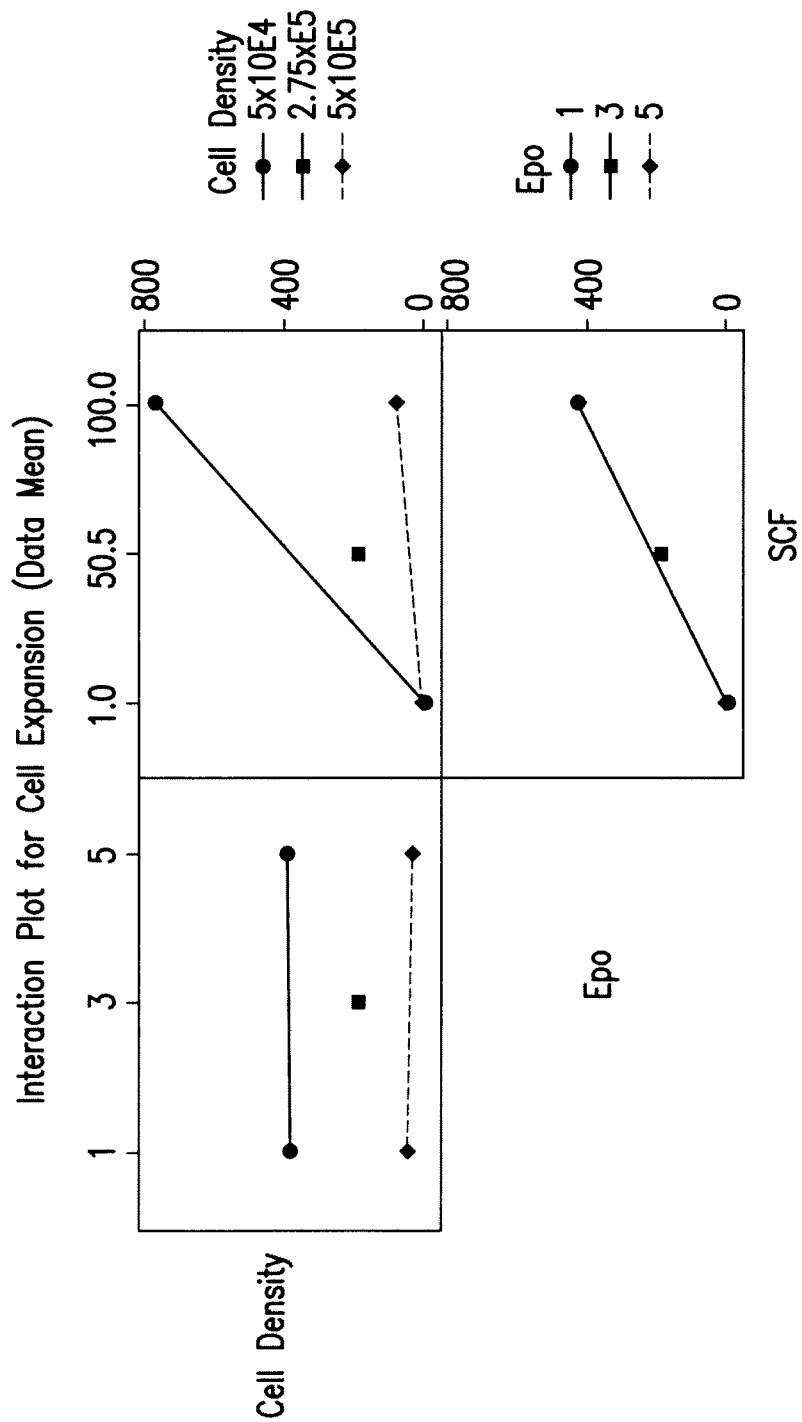
Figure 13C:
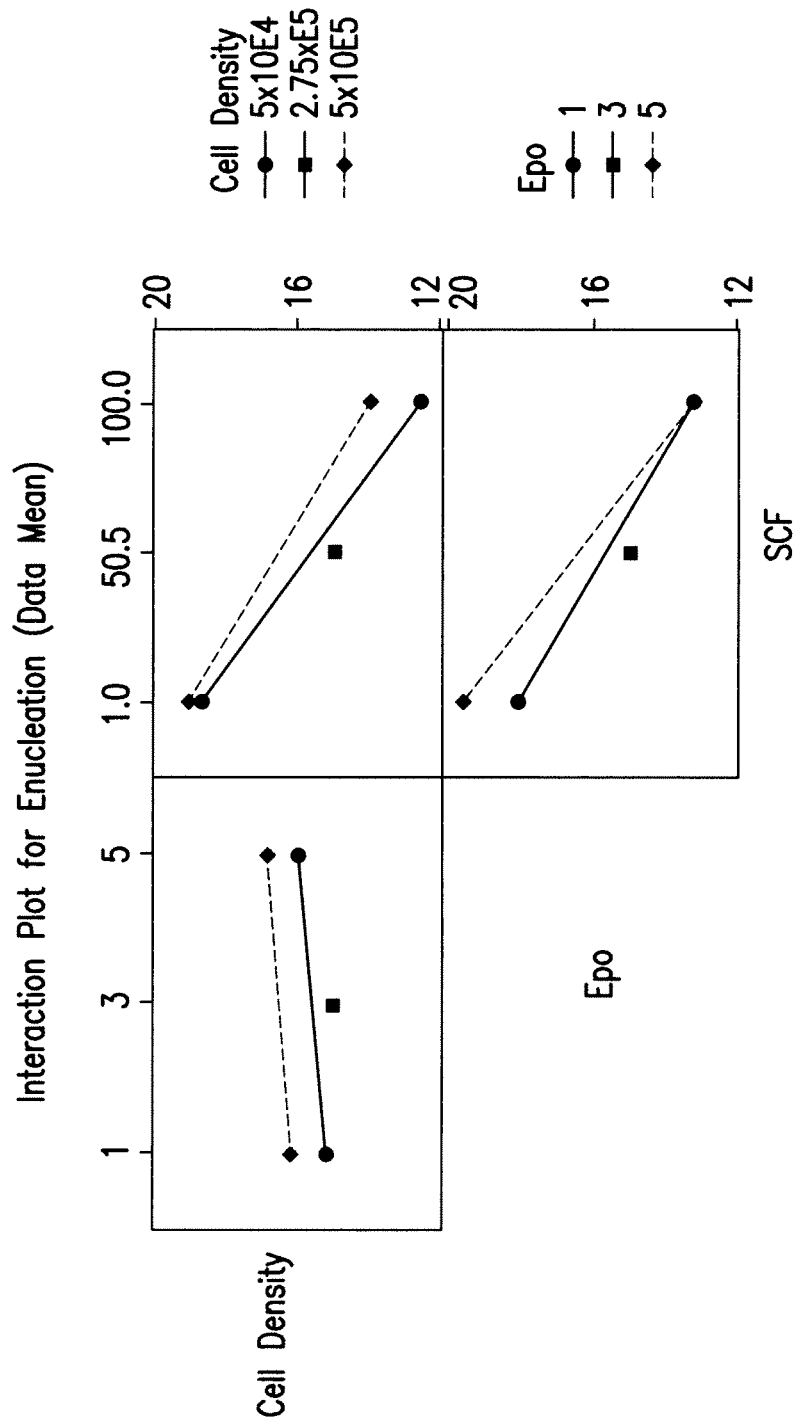

FIG. 13A-13C: 3-level DOE study to delineate interactions among SCF, Epo and cell density. FIG. 13A: Cube plot for factorial effects on cell expansion and differentiation; Interaction plots of SCF and cell density on cell expansion and differentiation at low cell density, high SCF concentration (FIG. 13B) or high cell density, low SCF concentration (FIG. 13C).

Figure 14:
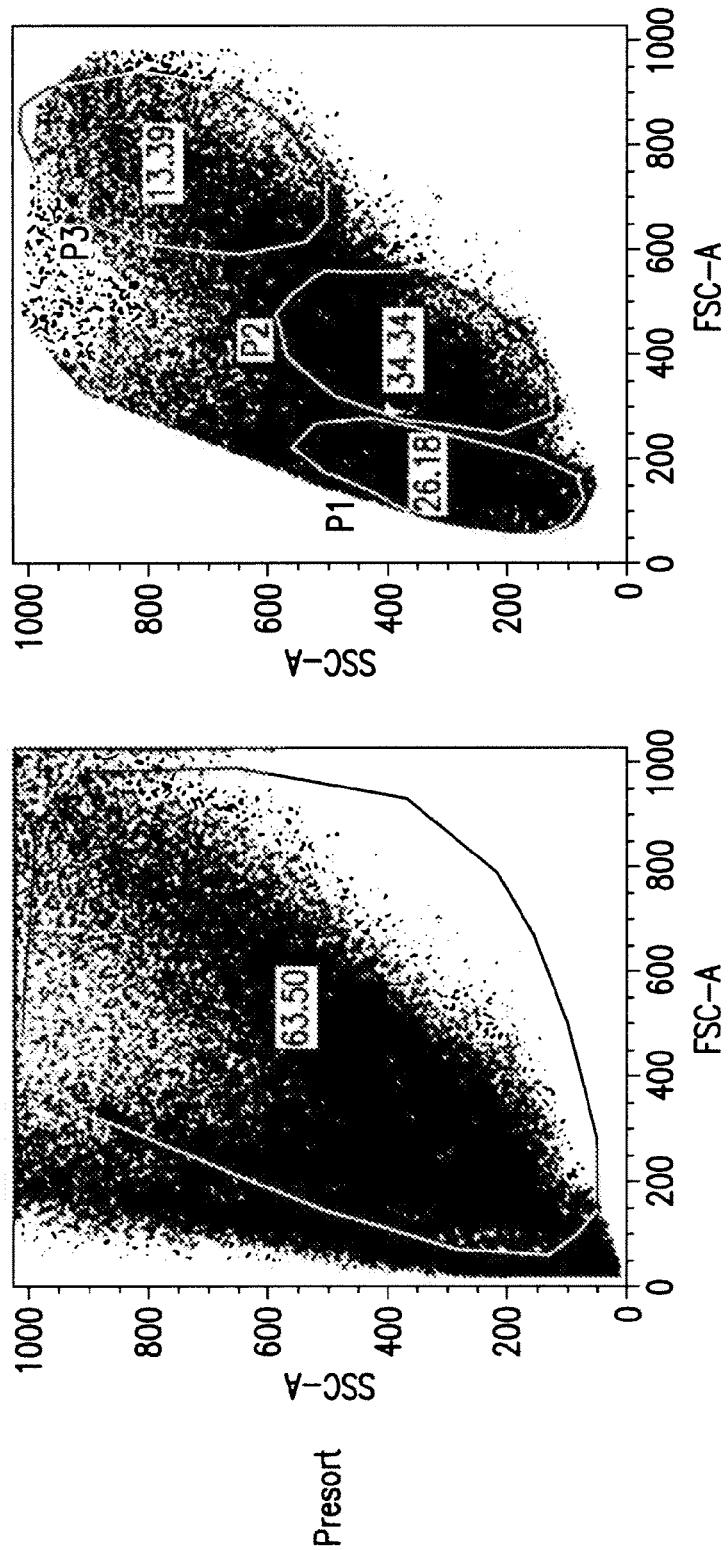

FIG. 14: Erythrocyte sorting by cell size. Erythrocyte population (P1) can be distinguished from other immature populations (P2 and P3) using forward (FSC) and side scatter (SSC).

Figure 15:
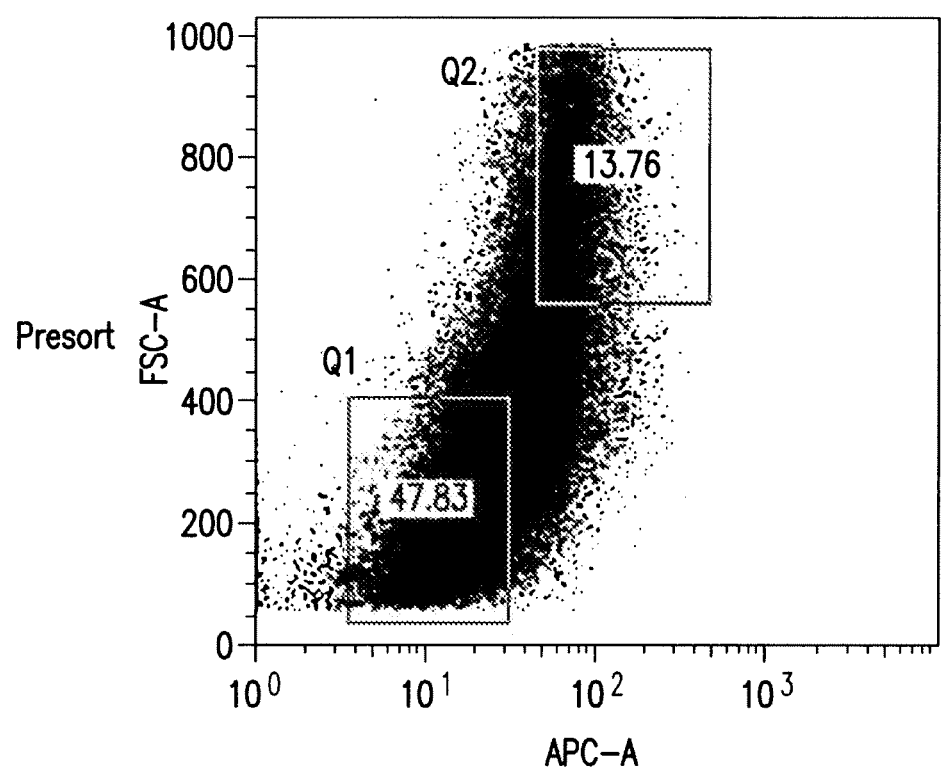

FIG. 15: Erythrocyte sorting by DRAQ staining.

5 DETAILED DESCRIPTION

Provided herein is a method of producing erythrocytes from expanded hematopoietic cells, e.g., hematopoietic stem cells and/or hematopoietic progenitor cells. In one embodiment, hematopoietic cells are collected from a source of such cells, e.g., placental perfusate, umbilical cord blood, placental blood, peripheral blood, and/or bone marrow. The hematopoietic cells are expanded and differentiated, continuously, without the use of feeder cells. Such isolation, expansion and differentiation can be performed in a central facility, which provides expanded hematopoietic cells tor shipment to decentralized expansion and differentiation at points of use, e.g., hospital, military base, military front line, or the like. Collection of erythrocytes produced in the method, in a preferred embodiment, is performed continuously or periodically, e.g., during differentiation. The continuous or periodic separation aspect of the method allows for the production of erythrocytes in a substantially smaller space than possible using, e.g., batch methods. The time for collection and expansion of the hematopoietic cells is approximately 5-10 days, typically about 7 days. The time for expansion and differentiation of the hematopoietic cells into erythrocytes is approximately 21-28 days. Erythrocytes, in certain embodiments, are then purified on-site and packaged into administrable units.

In one aspect, provided herein is a method of producing erythrocytes, comprising expanding a population of hematopoietic cells in a medium in the absence of feeder cells, wherein a plurality of hematopoietic cells within said population of hematopoietic cells differentiate info erythrocytes during said expanding; and isolating said erythrocytes from said medium, wherein said medium comprises SCF at a concentration of about 10 to about 10,000 ng/mL, IL-3 at a concentration of about 0.01 to about 500 ng/mL, and EPO at a concentration of about 0.1 to about 10 IU/mL, and wherein said SCF, IL-3 and Epo are not comprised within an undefined component of said medium (e.g., serum). In a specific embodiment, said isolating of erythrocytes in step (c) is performed continuously. In other specific embodiments, said isolating of erythrocytes in step (c) is performed periodically, e.g., every 1, 2, 3, 4, 5, 6, 7, 8, 9, 10, 15, 20, 25, 30, 35, 40, 45, 50, 55 or 60 minutes, or every 1, 1.5, 2, 2.5, 3, 3.5, 4, 4.5, 5, 5.5, 6, 6.5, 7.0, 7.5, 8.0, 8.5, 9.0, 9.5, 10.0, 10.5, 11.0, 11.5, 12, 13, 14, 15, 16, 17, 18, 19, 20, 21, 22, 23 or 24 hours, or more. In another specific embodiment, said isolating of erythrocytes in step (c) is performed periodically when one or more culture condition criteria are met, e.g., achievement in the culture of a particular cell density; achievement in the culture of a particular number of cells per milliliter expressing certain erythrocyte markers, e.g., CD36 or glycophorin A: or the like. The method of expanding and differentiating the hematopoietic cells is described in more detail in Section 5.2.2, below.

5.1. Hematopoietic Cells

Hematopoietic cells useful in the methods disclosed herein can be any hematopoietic cells able to differentiate into erythrocytes, e.g., precursor cells, hematopoietic progenitor cells, hematopoietic stem cells, or the like. Hematopoietic cells can be obtained from tissue sources such as, e.g., bone marrow, cord blood, placental blood, peripheral blood, or the like, or combinations thereof. Hematopoietic cells can be obtained from placenta. In a specific embodiment, the hematopoietic cells are obtained from placental perfusate. Hematopoietic cells from placental perfusate can comprise a mixture of fetal and maternal hematopoietic cells, e.g., a mixture in which maternal cells comprise greater than 5% of the total number of hematopoietic cells. Preferably, hematopoietic cells from placental perfusate comprise at least about 90%, 95%, 98%, 99% or 99.5% fetal cells.

In certain embodiments, the hematopoietic cells are $CD34^+$ cells. $CD34^+$ hematopoietic cells can, in certain embodiments, express or lack the cellular marker CD38. Thus, in specific embodiments, the hematopoietic cells useful in the methods disclosed herein are $CD34^+CD38^+$ or $CD34^+CD38^-$. In a more specific embodiment, the hematopoietic cells are $CD34^+CD38^-$ $Lin^-$. In another specific embodiment, the hematopoietic cell is one or more of $CD2^-$, $CD3^-$, $CD11b^-$, $CD11c^-$, $CD14^-$, $CD16^-$, $CD19^-$, $CD24^-$, $CD56^-$, $CD66b^-$ and glycophorin $A^-$. In another specific embodiment, the hematopoietic cell is $CD2^-$, $CD3^-$. $CD11b^-$, $CD11c^-$, $CD14^-$, $CD16^-$, $CD19^-$, $CD24^-$, $CD56^-$, $CD66b^-$ and glycophorin $A^-$. In other specific embodiments, the hematopoietic cells are $CD34^+$ and $CD133^+$; $CD34^+$ and $CD133^-$; $CD34^+$ and $CD117^+$; or $CD34^+$ and $CD117^-$. In another more specific embodiment, the hematopoietic cell is $CD34^+CD38^-CD33^-CD117^-$. In another more specific embodiment, the hematopoietic cell is $CD34^+CD38^-CD33^-CD117^-CD235^{-D}36^-$.

In another embodiment, the hematopoietic cells are $CD45^-$. In a specific embodiment, the hematopoietic cells are $CD34^+CD45^-$. In another specific embodiment, the hematopoietic cells are $CD34^+CD45^+$.

In another embodiment, the hematopoietic cell is $Thy-1^+$. In a specific embodiment, the hematopoietic cell is $CD34^+$ $Thy-1^+$. In another embodiment, the hematopoietic cells are $CD133^+$. In specific embodiments, the hematopoietic cells are $CD34^+CD133^+$ or $CD133^+Thy-1^+$. In another specific embodiment, the $CD34^+$ hematopoietic cells are $CXCR4^+$. In another specific embodiment, the $CD34^+$ hematopoietic cells are $CXCR4^-$. In another embodiment, the hematopoietic cells are positive for KDR (vascular growth factor receptor 2). In specific embodiments, the hematopoietic cells are $CD34^+KDR^+$, $CD133^+KDR^+$ or $Thy-1^+KDR^+$. In certain other embodiments, the hematopoietic cells are positive for aldehyde dehydrogenase ($ALDH^+$), e.g., the cells are $CD34^+$ $ALDH^+$.

In certain embodiments, the hematopoietic cells are $CD34^-$.

The hematopoietic cells can also lack certain markers that indicate lineage commitment, or a lack of developmental naiveté. For example, in another embodiment, the hematopoietic cells are $HLA-DR^+$. In specific embodiments, the hematopoietic cells are $CD34^+HLA-DR^-$, $CD133^+HLA-DR^-$, $Thy-1^+HLA-DR^-$ or $ALDH^+HLA-DR^-$. In another embodiment, the hematopoietic cells are negative for one or more, preferably all, of lineage markers CD2, CD3, CD11b, CD11c, CD14, CD16, CD19, CD24, CD56, CD66b and glycophorin A.

Thus, populations of hematopoietic cells can be selected for use in the methods disclosed herein on the basis of the presence of markers that indicate an undifferentiated state, or on the basis of the absence of lineage markers indicating that at least some lineage differentiation has taken place. Methods of isolating cells on the basis of the presence or absence of specific markers is discussed in detail, e.g., in Section 5.1.2, below.

Hematopoietic cells used in the methods provided herein can be a substantially homogeneous population, e.g., a population comprising at least about 95%, at least about 98% or at least about 99% hematopoietic cells from a single tissue source, or a population comprising hematopoietic cells exhibiting the same hematopoietic cell-associated cellular markers. For example, in various embodiment, the hematopoietic cells can comprise at least about 95%, 98% or 99% hematopoietic cells from bone marrow, cord blood, placental blood, peripheral blood, or placenta, e.g., placenta perfusate.

Hematopoietic cells used in the methods provided herein can be obtained from a single individual, e.g., from a single placenta, or from a plurality of individuals, e.g., can be pooled. Where the hematopoietic cells are obtained from a plurality of individuals and pooled, it is preferred that the hematopoietic cells be obtained from the same tissue source. Thus, in various embodiments, the pooled hematopoietic cells are all from placenta, e.g., placental perfusate, all from placental blood, all from umbilical cord blood, all from peripheral blood, and the like.

Hematopoietic cells used in the methods disclosed herein can comprise hematopoietic cells from two or more tissue sources. Preferably, when hematopoietic cells from two or more sources are combined for use in the methods herein, a plurality of the hematopoietic cells used to produce erythrocytes comprise hematopoietic cells from placenta, e.g., placenta perfusate. In various embodiments, the hematopoietic cells used to produce erythrocytes comprise hematopoietic cells from placenta and from cord blood; from placenta and peripheral blood; form placenta and placental blood, or placenta and bone marrow. In a preferred embodiment, the hematopoietic cells comprise hematopoietic cells from placental perfusate in combination with hematopoietic cells from cord blood, wherein the cord blood and placenta are from the same individual, i.e., wherein the perfusate and cord blood are matched. In embodiments in which the hematopoietic cells comprise hematopoietic cells from two tissue sources, the hematopoietic cells from the sources can be combined in a ratio of, for example, 1:10, 2:9, 3:8, 4:7, 5:6, 6:5, 7:4, 8:3, 9:2, 1:10, 1:9, 1:8, 1:7, 1:6, 1:5, 1:4, 1:3, 1:2, 1:1, 2:1, 3:1, 4:1, 5:1, 6:1, 7:1, 8:1 or 9:1.

Preferably, the erythrocytes produced from hematopoietic cells according to the methods provided herein are homogeneous with respect to blood type, e.g., identical with respect to cell surface markers, antigens, or the like. Such homogeneity can be achieved, for example, by obtaining hematopoietic cells from a single individual of the desired blood type. In embodiments in which hematopoietic cells are pooled from a plurality of individuals, it is preferred that each of the individuals shares at least one, at least two, or at least three or more antigenic blood determinants in common. In various embodiments, for example, the individual from which the hematopoietic cells are obtained is, or each of the individuals from which hematopoietic cells are obtained are, blood type O, blood type A, blood type B, or blood type AB. In other embodiments, the individual from which the hematopoietic cells are obtained is, or each of the individuals from which hematopoietic cells are obtained are, Rh positive, or Rh negative. In a specific embodiment, the individual from which the hematopoietic cells are obtained is, or each of the individuals from which hematopoietic cells are obtained are, O positive and Rh negative. In more specific embodiments, the individual from which the hematopoietic cells are obtained is, or each of the individuals from which hematopoietic cells are obtained are, O positive, O negative, A positive, A negative, B positive, B negative, AB positive, or AB negative. In other specific embodiments, the individual from which the hematopoietic cells are obtained is, or each of the individuals from which hematopoietic cells are obtained are, blood type M, blood type N, blood type S, or blood type s. In other specific embodiments, the individual from which the hematopoietic cells are obtained is, or each of the individuals from which hematopoietic cells are obtained are, blood type P1. In other specific embodiments, the individual from which the hematopoietic cells are obtained is, or each of the individuals from which hematopoietic cells are obtained are, blood type Lua, blood type Lub, or blood type Lu(a). In other specific embodiments, the individual from which the hematopoietic cells are obtained is, or each of the individuals from which hematopoietic cells are obtained are, blood type K (Kell), k (cellano), Kpa, Kpb, K(a+), Kp(a−b−) or K−k−Kp(a−b−). In other specific embodiments, the individual from which the hematopoietic cells are obtained is, or each of the individuals from which hematopoietic cells are obtained are, blood type Le(a−b−), Let(a+b−) or Le(a−b+). In other specific embodiments, the individual from which the hematopoietic cells are obtained is, or each of the individuals from which hematopoietic cells are obtained are, blood type Fy a, Fy b or Fy(a−b−). In other specific embodiments, the individual from which the hematopoietic cells are obtained is, or each of the individuals from which hematopoietic cells are obtained are, blood type Jk(a−b−), Jk(a+b−), Jk(a−b+) or Jk(a+b+). In other specific embodiments, the individual from whom the hematopoietic cells are obtained is classifiable within blood group Diego, Cartwright, Xgm Scianna, Bombrock, Colton, Lansteiner-Weiner, Chido/Rogers, Hh, Kx, Gergich, Cromer, Knops, Indian, Ok, Raph, or JMH. In other specific embodiments, each of the individuals from which hematopoietic cells are obtained are of the same blood type within a blood typing system or group of antigenic determinants, wherein said blood typing system or group of antigenic determinants are Diego, Cartwright, Xgm Scianna, Bombrock, Colton, Lansteiner-Weiner, Chido/Rogers, Hh, Kx, Gergich, Cromer, Knops, Indian, Ok, Raph, or JMH.

5.1.1. Placental Hematopoietic Stem Cells

In certain embodiments, the hematopoietic cells used in the methods provided herein are placental hematopoietic cells. As used herein, "placental hematopoietic cells" means hematopoietic cells obtained from the placenta itself, and not from placental blood or from umbilical cord blood. In one embodiment, placental hematopoietic cells are $CD34^+$. In a specific embodiment, the placental hematopoietic cells are predominantly (e.g., at least about 50%, 55%, 60%, 65%, 70%, 75%, 80%, 85%, 90%, 95% or 98%) $CD34^+TD38^-$ cells. In another specific embodiment, the placental hematopoietic cells are predominantly (e.g., at least about 50%, 55%, 60%, 65%, 70%, 75%, 80%, 85%, 90%, 95% or 98%) $CD34^+CD38^+$ cells. Placental hematopoietic cells can be obtained from a post-partum mammalian (e.g., human) placenta by any means known to those of skill in the art, e.g., by perfusion.

In another embodiment, the placental hematopoietic cell is $CD45^-$. In a specific embodiment, the hematopoietic cell is $CD34^+CD45^-$. In another specific embodiment, the placental hematopoietic cells are $CD34^+CD45^+$.

5.1.1.1. Obtaining Placental Hematopoietic Cells by Perfusion

Placental hematopoietic cells can be obtained using perfusion. Methods of perfusing mammalian placenta to obtain cells, including placental hematopoietic cells, are disclosed, e.g. In U.S. Pat. No. 7,045,148, entitled "Method of Collecting placental Stem Cells," U.S. Pat. No. 7,255,879, entitled "Post-Partum Mammalian Placenta, Its Use and Placental Stem Cells Therefrom," and in U.S. Application No. 2007/0190042, entitled "Improved Medium for Collecting Placental Stem Cells and Preserving Organs," the disclosures of which are hereby incorporated by reference in their entireties.

Placental hematopoietic cells can be collected by perfusion, e.g., through the placental vasculature, using, e.g., a saline solution (for example, phosphate-buffered saline, a 0.9% NaCl solution, or the like), culture medium or organ preservation solution as a perfusion solution. In one embodiment, a mammalian placenta is perfused by passage of perfusion solution through either or both of the umbilical artery and umbilical vein. The flow of perfusion solution through the placenta may be accomplished using, e.g., gravity flow into the placenta. Preferably, the perfusion solution is forced through the placenta using a pump, e.g., a peristaltic pump. The umbilical vein can be, e.g., cannulated with a cannula, e.g., a TEFLON® or plastic cannula, which is connected to a sterile connection apparatus, such as sterile tubing, which, in turn is connected to a perfusion manifold.

In preparation for perfusion, the placenta is preferably oriented (e.g., suspended) in such a manner that the umbilical artery and umbilical vein are located at the highest point of the placenta. The placenta can be perfused by passage of a perfusion fluid through the placental vasculature and surrounding tissue. The placenta can also be perfused by passage of a perfusion fluid into the umbilical vein and collection from the umbilical arteries, or passage of a perfusion fluid into the umbilical arteries and collection from the umbilical vein.

In one embodiment, for example, the umbilical artery and the umbilical vein are connected simultaneously, e.g., to a pipette that is connected via a flexible connector to a reservoir of the perfusion solution. The perfusion solution is passed into the umbilical vein and artery. The perfusion solution exudes from and/or passes through the walls of the blood vessels into the surrounding tissues of the placenta, and is collected in a suitable open vessel, e.g., a sterile pan, from the surface of the placenta that was attached to the uterus of the mother during gestation. The perfusion solution may also be introduced through the umbilical cord opening and allowed to flow or percolate out of openings in the wall of the placenta which interfaced with the maternal uterine wall. Placental cells that are collected by this method, which can be referred to as a "pan" method, are typically a mixture of fetal and maternal cells.

In another embodiment, the perfusion solution is passed through the umbilical veins and collected from the umbilical artery, or is passed through the umbilical artery and collected from the umbilical veins. Placental cells collected by this method, which can be referred to as a "closed circuit" method, are typically almost exclusively fetal.

The closed circuit perfusion method can, in one embodiment, be performed as follows. A post-partum placenta is obtained within about 48 hours after birth. The umbilical cord is clamped and cut above the clamp. The umbilical cord can be discarded, or can processed to recover, e.g., umbilical cord stem cells, and/or to process the umbilical cord membrane for the production of a biomaterial. The amniotic membrane can be retained during perfusion, or can be separated from the chorion, e.g., using blunt dissection with the fingers. If the amniotic membrane is separated from the chorion prior to perfusion, it can be, e.g., discarded, or processed, e.g., to obtain stem cells by enzymatic digestion, or to produce, for example, an amniotic membrane biomaterial, e.g., the biomaterial described in U.S. Application Publication No. 2004/0048796, the disclosure of which is hereby incorporated by reference in its entirety.

After cleaning the placenta of all visible blood clots and residual blood, e.g., using sterile gauze, the umbilical cord vessels are exposed, e.g., by partially cutting the umbilical cord membrane to expose a cross-section of the cord. The vessels are identified, and opened, e.g., by advancing a closed alligator clamp through the cut end of each vessel. The apparatus, e.g., plastic tubing connected to a perfusion device or peristaltic pump, is then inserted into each of the placental arteries. The pump can be any pump suitable for the purpose, e.g., a peristaltic pump. Plastic tubing, connected to a sterile collection reservoir, e.g., a blood bag such as a 250 mL collection bag, is then inserted into the placental vein. Alternatively, the tubing connected to the pump is inserted into the placental vein, and tubes to a collection reservoir(s) are inserted into one or both of the placental arteries. The placenta is then perfused with a volume of perfusion solution, e.g., about 750 ml of perfusion solution. Cells in the perfusate are then collected, e.g., by centrifugation.

In one embodiment, the proximal umbilical cord is clamped during perfusion, and more preferably, is clamped within 4-5 cm (centimeter) of the cord's insertion into the placental disc.

The first collection of perfusion fluid from a mammalian placenta during the exsanguination process is generally colored with residual red blood cells of the cord blood and/or placental blood. The perfusion fluid becomes more colorless as perfusion proceeds and the residual cord blood cells are washed out of the placenta. Generally from 30 to 100 ml (milliliter) of perfusion fluid is adequate to initially exsanguinate the placenta, but more or less perfusion fluid may be used depending on the observed results.

The volume of perfusion liquid used to collect placental hematopoietic cells may vary depending upon the number of hematopoietic cells to be collected, the size of the placenta, the number of collections to be made from a single placenta, etc. In various embodiments, the volume of perfusion liquid may be from 50 mL to 5000 mL, 50 mL to 4000 mL, 50 mL to 3000 mL, 100 mL to 2000 mL, 250 mL to 2000 mL, 500 mL to 2000 mL, or 750 mL to 2000 mL. Typically, the placenta is perfused with 700-800 mL of perfusion liquid following exsanguination.

The placenta can be perfused a plurality of times over the course of several hours or several days to obtain placental hematopoietic cells. Where the placenta is to be perfused a plurality of times, it may be maintained or cultured under aseptic conditions in a container or other suitable vessel, and perfused with a stem cell collection composition (see U.S. Application Publication No, 2007/0190042, the disclosure of which is incorporated herein by reference in its entirety), or a standard perfusion solution (e.g., a normal saline solution such as phosphate buffered saline ("PBS")) with or without an anticoagulant (e.g., heparin, warfarin sodium, coumarin, bishydroxycoumarin), and/or with or without an antimicrobial agent (e.g., β-mercaptoethanol (0.1 mM); antibiotics such as streptomycin (e.g., at 40-100 μg/ml), penicillin (e.g., at 40 U/ml), amphotericin B (e.g., at 0.5 μg/ml). In one embodiment, an isolated placenta is maintained or cultured for a period of time without collecting the perfusate, such that the placenta is maintained or cultured for 1, 2, 3, 4, 5, 6, 7, 8, 9, 10, 11, 12, 13, 14, 15, 16, 17, 18, 19, 20, 21, 22, 23, or 24 hours, or 2 or 3 or more days before perfusion and collection of perfusate. The perfused placenta can be maintained for one or more additional time(s), e.g., 1, 2, 3, 4, 5, 6, 7, 8, 9, 10, 11, 12, 13, 14, 15, 16, 17, 18, 19, 20, 21, 22, 23, 24 or more hours, and perfused a second time with, e.g., 700-800 mL perfusion fluid. The placenta can be perfused 1, 2, 3, 4, 5 or more times, for example, once every 1, 2, 3, 4, 5 or 6 hours. In a preferred embodiment, perfusion of the placenta and collection of perfusion solution, e.g., stem cell collection composition, is repeated until the number of recovered nucleated cells falls below 100 cells/ml. The perfusates at different time points can be further processed individually to recover time-dependent populations of cells, e.g., placental hematopoietic cells. Perfusates from different time points can also be pooled.

5.1.1.2. Obtaining Placental Hematopoietic Cells by Tissue Disruption

Hematopoietic cells can be isolated from placenta by perfusion with a solution comprising one or more proteases or other tissue-disruptive enzymes (e.g., trypsin, collagenase, papain, chymotrypsin, subtilisin, hyaluronidase; a cathepsin, a caspase, a calpain, chymosin, plasmepsin, pepsin, or the like). In a specific embodiment, a placenta or portion thereof (e.g., amniotic membrane, amnion and chorion, placental lobule or cotyledon, umbilical cord, or combination of any of the foregoing) is brought to 25° C.-37° C., and is incubated with one or more tissue-disruptive enzymes in 200 mL of a culture medium for 30 minutes. Cells from the perfusate are collected, brought to 4° C., and washed with a cold inhibitor mix comprising 5 mM EDTA, 2 mM dithiothreitol and 2 mM beta-mercaptoethanol. The stem cells are washed alter several minutes with cold (e.g., 4° C.) stem cell collection composition.

In one embodiment, the placenta can be disrupted mechanically (e.g., by crushing, blending, dicing, mincing or the like) to obtain the hematopoietic cells. The placenta can be used whole, or can be dissected into components prior to physical disruption and/or enzymatic digestion and hematopoietic cell recovery. For example, hematopoietic cells can be obtained from the amniotic membrane, chorion, umbilical cord, placental cotyledons, or any combination thereof.

Placental hematopoietic cells can also be obtained by enzymatic disruption of the placenta using a tissue-disrupting enzyme, e.g., trypsin, collagenase, papain, chymotrypsin, subtilisin, hyaluronidase; a cathepsin, a caspase, a calpain, chymosin, plasmepsin, pepsin, or the like. Enzymatic digestion preferably uses a combination of enzymes, e.g., a combination of a matrix metalloprotease and a neutral protease, for example, a combination of collagenase and dispose. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Any combination of tissue digestion enzymes can be used. Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental stem cells. For example, in one embodiment, a placenta or part thereof, is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N'N'-tetraacetic acid (EGTA) or ethylenediaminetetraacetic acid (EDTA) to the stem cell collection composition comprising the stem cells, or to a solution in which the tissue is disrupted and/or digested prior to isolation of the placental hematopoietic cells.

It will be appreciated that where an entire placenta, or portion of a placenta comprising both fetal and maternal cells (for example, where the portion of the placenta comprises the chorion or cotyledons), the placental hematopoietic cells collected will comprise a mix of placental stem cells derived from both fetal and maternal sources. Where a portion of the placenta that comprises no, or a negligible number of, maternal cells (for example, amnion), the placental stem cells collected will comprise almost exclusively fetal placental stem cells.

5.1.2 Isolation, Sorting, and Characterization of Cells

Cells, including hematopoietic cells from any source, e.g., mammalian placenta, can initially be purified from (i.e., be isolated from) other cells by, e.g., Ficoll gradient centrifugation, hetastarch treatment or ammonium chloride treatment. Centrifugation, e.g., Ficoll (e.g., from GE Healthcare, Cat. No. 17-1440-03) centrifugation, can follow any standard protocol for centrifugation speed, etc. In one embodiment, for example, cells collected from the placenta are recovered from perfusate by centrifugation at 150×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at about 22° C., and the low-density interface layer of cells is collected for further processing.

In a specific, non-limiting embodiment, hetastarch (e.g., HetaSep, Stem Cell Technologies, Catalog No. 07906) treatment can be performed by adding 1 part hetastarch solution to 5 parts, e.g., human placental perfusate (HPP) or cord blood in an appropriately sized tube. After mixing well, samples are allowed to settle until the plasma/RBC interface is at approximately 50% of the total volume. Optionally, placing the tube in a 37° C. incubator for this step increases the sedimentation rate. A defined interface forms between the RBC fraction and the RBC-depleted (nucleated cell-rich) fraction as the RBC sediment through the hetastarch solution. The leukocyte-rich layer is then harvested and placed in a 50 mL tube. This fraction is washed once with, e.g., at least a four-told volume of appropriate medium. A slow spin is performed to remove platelets by centrifuging at, e.g., 120×g for 10 minutes at room temperature (15-25° C. with no brake. In certain other embodiments, ammonium chloride (e.g., Stem Cell Technologies, Catalog No. 07850) treatment can be performed by adding buffered ammonium chloride solution ($NH_4Cl$) to HPP or cord blood e.g. at a volume: volume ratio of about 4:1. Vortex the cell suspension and place on ice for 10 minutes to allow erythrocytes to lyse. Cells are optionally washed twice in the appropriate medium prior to use.

Cell pellets can be resuspended in, e.g., fresh saline solution, or a medium suitable for stem cell maintenance, e.g., IMDM serum-free medium containing 2 U/ml heparin and 2 mM EDTA (GibcoBRL, N.Y.). The total mononuclear cell fraction can be isolated, e.g., using LYMPHOPREP® (Nycomed Pharma Oslo, Norway) according to the manufacturer's recommended procedure.

As used herein, "isolating" cells, including placental cells, e.g., placental hematopoietic cells or placental stem cells, means to remove at least about 20%, 30%, 40%, 50%, 60%, 70%, 80%, 90%, 95% or 99% of the cells with which the isolated cells are normally associated in the intact tissue, e.g., mammalian placenta. A cell from an organ is "isolated" when the cell is present in a population of cells that comprises fewer than 50% of the cells with which the stem cell is normally associated in the intact organ.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell soiling (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34, in an assay such as an ELISA or RIA, or by FACS; if so, the cell is $CD34^+$. Similarly, if a cell, produces enough RNA encoding, e.g., OCT-4 to be detectable by RT-PCR, the ceil is $OCT-4^+$. Antibodies to cell surface markers (e.g., CD markers such as CD34) and the sequence of stem cell-specific genes, such as OCT-4, are well-known in the art.

Placental cells, particularly cells that have been isolated, e.g., by Ficoll separation, hetastarch treatment, ammonium chloride treatment, differential adherence, or a combination of both, may be sorted using fluorescence activated cell sorting (FACS). FACS is a well-known method for separating particles, including cells, based on the fluorescent properties of the particles (Kamareh, 1987, Methods Enzymol, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one embodiment, stem cells from placenta are sorted, e.g., isolated, on the basis of expression one or more of the markers CD34, CD38, CD44, CD45, CD73, CD105, CD117, CD200, OCT-4 and/or HLA-G.

In another embodiment, hematopoietic cells, e.g., $CD34^+$, $CD133^+$, $KDR^+$ or $Thy-1^+$ cells, are sorted, e.g., isolated, on the basis of markers characteristic of undifferentiated hematopoietic cells. Such sorting can be done, e.g., in a population of cells that has not been sorted, e.g., a population of cells from a perfusion or a tissue digestion, wherein $CD34^+$ cells represent a minority of the cells present in the population. Such sorting can also be done in a population of cells that is mostly (e.g., greater than 50%, 60%, 70%, 80%, 90%, 95%, 98% or 99%) hematopoietic cells as, for example, a purification step. For example, in a specific embodiment, $CD34^+$ cells, $KDR^+$ cells, $Thy-1^+$ cells, and/or $CD133^+$ cells are retained during sorting to produce a population of undifferentiated hematopoietic cells.

In another embodiment, cells, e.g., hematopoietic cells are soiled, e.g., excluded, on the basis of markers of lineage-differentiated cells. For example, cells, in a population of hematopoietic cells, that are $CD2^+$, $CD3^+$, $CD11b^+$, $CD11c^+$, $CD14^+$, $CD16^+$, $CD19^+$, $CD24^+$, $CD56^+$, $CD66b^+$ and/or glycophorin $A^+$ are excluded during sorting from the population of hematopoietic cells to produce a population of undifferentiated hematopoietic cells.

In another embodiment, hematopoietic cells can be sorted, e.g., isolated, on the basis of lack of expression of, e.g., lineage markers. In a specific embodiment, for example, hematopoietic cells, e.g., $CD34^+$ cells, can be isolated based on a determination that the cells are one or more of $CD2^-$, $CD3^-$, $CD11b^-$, $CD11c^-$, $CD14^-$, $CD16^-$, $CD19^-$, $CD24^-$, $CD56^-$, $CD66b^-$ and/or glycophorin $A^-$.

In another embodiment, magnetic beads can be used to separate cells, e.g., DYNABEADS® (Invitrogen). The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microliter dishes for clonal isolation.

In another embodiment, placental stem cells, e.g., placental hematopoietic cells or adherent placental stem cells, can be identified and characterized by a colony forming unit assay. Colony forming unit assays are commonly known in the art, such as MESENCULT™ medium (Stem Cell Technologies, Inc., Vancouver British Columbia).

Placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Placental stem ceils can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

5-2. Expansion of Hematopoietic Cells

Once a population of hematopoietic cells is obtained, the population is expanded. One unit of erythrocytes is expected to comprise about 1-2×10$^{12}$ red blood cells. Hematopoietic stem cell population doubling requires approximately 36 hours. Thus, starting from about 5×10$^7$ hematopoietic cells according to standard methods, and assuming 100% efficiency in expansion and differentiation, production of a unit of erythrocytes would require approximately 14 hematopoietic cell population doublings, or approximately 3 weeks. The method described in detail below improves on standard methods by improving the culture conditions of hematopoietic cells and increasing the number of hematopoietic cells during expansion per unit time.

5.2.1. Shortened Hematopoietic Cell Expansion Time

Cells, including hematopoietic cells, comprise cell cycle control mechanisms, which include cyclins and eyelin-dependent kinases (CDKs), that control the rate of cell division. Cell cycle checkpoints are used by cells to monitor and regulate the progress of the cell cycle. If a cell fails to meet the requirements of a phase it will not be allowed to proceed to the next phase until the requirements have been met. The processes associated with qualifying the cell for progression through the different phases of the cell cycle (checkpoint regulation) are relatively slow and contribute to the relatively modest rate of cell division observed in mammalian cells, even under optimal in vitro culture conditions.

In one embodiment of the method of producing erythrocytes, the method uses hematopoietic cells that have a reduced population doubling time. In a specific embodiment, the hematopoietic cells are modified to express higher-than-normal levels of a cell cycle activator, or a lower-than-normal level of a cell cycle inhibitor, wherein the engineered cells have a detectably shorter doubling time than unmodified hematopoietic cells. In a more specific embodiment, the hematopoietic cells are modified to express a higher-than-normal level of one or more of the cell cycle activator cyclin T2 (CCNT2), cyclin T2B (CCNT2B), CDC7L1, CCN1, cyclin G (CCNG2), cyclin H (CCNH), CDKN2C, CDKN2D, CDK4, cyclin D1, cyclin A, cyclin B, Hes1, Hox genes and/or FoxO.

In another more specific embodiment, the hematopoietic cells express a lower-than-normal level of CDK inhibitors p21, p27 and/or TReP-132. Reduction of expression of CDK inhibitors can be accomplished by any means known in the art, e.g., the use of small molecule inhibitors, antisense oligonucleotides targeted to a p21, p27 and/or TReP-132 DNA, pre-mRNA or mRNA sequence, RNAi, or the like.

Modifications of hematopoietic progenitor cells in the context of the present method of producing erythrocytes are expected to be safe in a therapeutic context, as erythrocytes are enucleated and incapable of replication.

In another specific embodiment, the hematopoietic cells are modified to express higher-than-normal levels of a cell cycle activator, wherein the engineered cells have a detectably shorter doubling time than, or detectably increased rate of proliferation compared to, unmodified hematopoietic cells, and where the increased expression of a cell cycle activator is inducible. Any inducible promoter known in the art can be used to construct such a modified hematopoietic cell, e.g., a tetracycline-inducible gene expression system using a stably expressed reverse tetracyeline-controlled transactivator (rtTA) under the control of a CMV promoter (e.g., REVTET-ON® System, Clontech Laboratories, Palo Alto, Calif.); U.S. Patent Application Publication No. 2007/0166366 "Autologous Upregulation Mechanism Allowing Optimized Cell Type-Specific and Regulated Gene Expression Cells"; and U.S. Patent Application Publication No. 2007/0122880 "Vector for the Inducible Expression of Gene Sequences," the disclosure of each of which is incorporated herein by reference in its entirety.

Expression of a gene encoding a cell cycle inhibitor or negative cell cycle regulator can be disrupted in a hematopoietic cell, e.g., by homologous or non-homologous recombination using standard methods. Disruption of expression of a cell cycle inhibitor or negative cell cycle regulator can also be effected, e.g., using an antisense molecule to, e.g., p21, p27 and/or TReP-132.

In another embodiment, hematopoietic cells used to produce erythrocytes are modified to express notch 1 ligand such that expression of the notch 1 ligand results in detectably decreased senescence of the hematopoietic cells compared to unmodified hematopoietic cells; see Berstein et al., U.S. Patent Application Publication 2004/0067583 "Methods for Immortalizing Cells," the disclosure of which is incorporated herein by reference in its entirety.

In another specific embodiment, the medium in which the hematopoietic cells are expanded enhance faithful DNA replication, e.g., the medium includes one or more antioxidants.

In a preferred embodiment, the method of producing erythrocytes includes a step that excludes any modified hematopoietic cells, or pre-erythrocyte precursors, from the final population of isolated erythrocytes produced in the method disclosed herein. Such separation can be accomplished as described elsewhere herein on the basis of one or more markers characteristic of hematopoietic cells not fully differentiated into erythrocytes. The exclusion step can be performed subsequent to an isolation step in which erythrocytes are selected on the basis of erythrocyte-specific markers, e.g., CD36 and/or glycophorin A.

5.2.2. Feeder Cell-Independent Expansion and Differentiation of Hematopoietic Cells In certain embodiments, hematopoietic cells, e.g., stem cells or progenitor cells, used in the methods provided herein are expanded and differentiated in culture without the use of a feeder layer. Culture of the hematopoietic cells as provided herein results in continuous expansion of the hematopoietic cells and differentiation of erythrocytes from said cells.

Feeder cell-independent expansion and differentiation of hematopoietic cells can take place in any container compatible with cell culture and expansion, e.g., flask, tube, beaker, dish, multiwell plate, bag or the like. In a specific embodiment, feeder cell-independent expansion of hematopoietic cells takes place in a bag. e.g., a flexible, gas-permeable fluorocarbon culture bag (for example, from American Fluoroseal). In a specific embodiment, the container in which the hematopoietic cells are expanded is suitable for shipping, e.g., to a site such as a hospital or military zone wherein the expanded hematopoietic cells are further expanded and differentiated, e.g., using the bioreactor described below.

In certain embodiments, hematopoietic cells, in certain embodiments, are expanded and differentiated, in continuous fashion, in a culture medium comprising stem cell factor (SCF), erythropoietin (Epo), and interleukin-3 (IL-3).

Thus, in one aspect, provided herein is a method of producing erythrocytes, comprising expanding and differentiating a population of hematopoietic cells in a medium in the absence of feeder cells, wherein a plurality of hematopoietic cells within said population of hematopoietic cells differentiate into erythrocytes during said expanding;

and isolating said erythrocytes from said medium, wherein said medium comprises SCF at a concentration of about 10 to about 10,000 ng/mL. IL-3 at a concentration of about 0.01 to about 500 ng/mL, and EPO at a concentration of about 0.1 to about 10 IU/mL, and wherein said SCF, IL-3 and Epo are not comprised within an undefined component of said medium (e.g., serum). In a specific embodiment of the method, said medium does not comprise one or more, or any, of Flt-3L, IL-11, thrombopoietin (Tpo), homcobox-B4 (HoxB4), or methylcellulose. In other specific embodiments, said medium comprises SCF at a concentration of about 20 to about 2000 ng/mL; about 50 to about 1000 ng/mL; or about 100 ng/mL. In other specific embodiments, said medium comprises IL-3 at a concentration of about 0.1 to about 100 ng/mL; about 1 to about 50 ng/mL; or about 5 ng/mL. In other specific embodiments, said medium comprises EPO at a concentration of about 1 to about 5 IU/mL; or about 2 to about 3 IU/mL.

In certain embodiments, the medium facilitates the expansion of hematopoietic stem cells in culture, e.g., $CD34^+$ hematopoietic stem cells, wherein the cells are seeded at $5\times10^5$ cells/mL or less, $2.75\times10^4$ cells/mL or less, or $5\times10^4$ cells/mL or less; wherein Epo is present (e.g., the medium comprises) 5 IU/ml or less, 3 IU/mL or less, or 1 IU/mL or less; and SCF is present (e.g., the medium comprises) at 1 ng/mL or more, 50 ng/mL or more, or 100 ng/mL or more. In a specific embodiment, the cells are seeded at $5\times10^4$ cells/mL or less, and the medium comprises 1 IU/mL or less Epo and 100 ng/mL or more SCF.

In another specific embodiment of the method, said medium further comprises insulin-like growth factor 1 (IGF-1) at a concentration of about 1 to about 1000 ng/mL and lipids at a concentration of about 1 to about 1000 μg/mL, wherein said lipids comprise a mixture of protein and cholesterol (e.g., Lipids Cholesterol enriched from adult bovine serum; Cat. No. C7305-1G, Sigma, St Louis, Mo.); and wherein said medium comprises hydrocortisone at a concentration of about 0.01 to about 100 μM, or dexamethasone at a concentration of about 0.01 μM to about 100 μM. In more specific embodiments, said medium comprises IGF-1 at a concentration of about 10 to about 500 ng/mL; or about 20 to about 100 ng/mL. In other more specific embodiments, said medium comprises lipids at a concentration of about 10 to about 500 ng/mL; or about 20 to about 100 ng/mL. In other more specific embodiments, said medium comprises hydrocortisone at a concentration of about 0.1 to about 50 μM; or about 0.5 to about 10 μM. In other more specific embodiments, said medium comprises dexamethasone at a concentration of about 0.05 to about 20 μM; or about 0.1 to about 10 μM.

In a more specific embodiment of the method, the medium comprises about 100 ng/mL SCF, about 3 U/mL Epo, about 40 ng/mL IGF-1, about 5 ng/mL IL-3, about 1 μM Dexamethasone, and 40 μg/ml lipids, wherein said lipids comprise a mixture of protein and cholesterol. In another more specific embodiment of the method, the medium comprises about 100 ng/mL SCF, about 2 U/mL Epo, about 40 ng/mL IGF-1, about 5 ng/mL IL-3, about 1 μM hydrocortisone, and 50 ng/ml lipids, wherein said lipids comprise a mixture of protein and cholesterol.

In certain other embodiments, hematopoietic cells, in certain embodiments, are expanded and differentiated, in continuous fashion, in a culture medium comprising SCF; Epo; IGF-1; lipids, wherein the lipids comprise a mixture of proteins and cholesterol (e.g., Lipids Cholesterol Rich from adult bovine serum; Cat. No. C7305-1G. Sigma. St Louis. Mo.); and either hydrocortisone or dexamethasone. In specific embodiments, said medium comprises SCF at a concentration of about 10 to about 10,000 ng/mL; about 20 to about 2000 ng/mL; about 50 to about 1000 ng/mL; about 100 ng/mL; or about 100 ng/mL. In other specific embodiments, said medium comprises Epo at a concentration of about 1 to about 5 IU/mL; or about 2 to about 3 IU/mL. In other specific embodiments, said medium comprises IGF-1 at a concentration of about 1 to about 1000 ng/mL; about 10 to about 500 ng/mL; about 20 to about 100 ng/mL; or about 40 ng/mL. In other specific embodiments, said medium comprises said lipids at a concentration of about 1 to about 1000 μg/mL; about 10 to about 500 ng/mL; about 20 to about 100 ng/mL; or about 40 ng/mL. In other specific embodiments, said medium comprises hydrocortisone at a concentration of about 0.1. μM to about 10 μM; about 0.5 μM to about 5 μM; or about 1 μM. In other specific embodiments, said medium comprises dexamethasone at a concentration of about 0.1 μM to about 10 μM; about 0.5 μM to about 5 μM; or about 1 μM.

In addition to the method, provided herein are any of the media described above as compositions. In certain embodiments of any of the methods or compositions provided herein, the medium can be a serum-free medium, e.g., STEMSPAN® (Cat. No. 09650, Stem Cell Technologies, Vancouver, Canada).

In another embodiment, hematopoietic cells are expanded by culturing said cells in contact with an immunomodulatory compound, e.g., a TNF-α inhibitory compound, for a time and in an amount sufficient to cause a detectable increase in the proliferation of the hematopoietic cells over a given time, compared to an equivalent number of hematopoietic cells not contacted with the immunomodulatory compound. See. e.g., U.S. Patent Application Publication No. 2003/0235909, the disclosure of which is hereby incorporated by reference in its entirety. In a preferred embodiment, the immunomodulatory compound is 3-(4-amino-1-oxo-1,3-dihydroisoindol-2-yl)-piperidine-2,6-dione; 3-(4'aminoisolindoline-1'-one)-1-piperidine-2,6-dione; 4-(amino)-2-(2,6-dioxo(3-piperidyl))-isoindoline-1,3-dione; 4-amino-2-[(3RS)-2,6-dioxopiperidin-3-yl]-2H-isoindole-1,3-dione; α-(3-aminophthalimido) glutarimide; pomalidomide, lenalidomide, or thalidomide. In another embodiment, said immunomodulatory compound is a compound having the structure

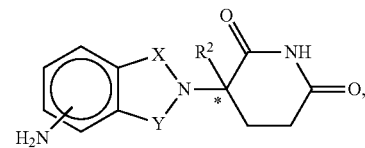

wherein one of X and Y is OCX the other of X and Y is C=O or $CH_2$, and $R^2$ is hydrogen or lower alkyl, or a pharmaceutical acceptable salt, hydrate, solvate, clathrate, enantiomer, diastereomer, racemate, or mixture of stereoisomers thereof. In another embodiment, said immunomodulatory compound is a compound having the structure

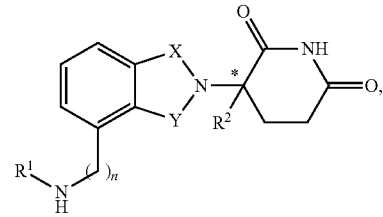

wherein one of X and Y is C=O and the other is CH$_2$ or C=O;

R$^1$ is H, (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, C(O)R$^3$, C(S)R$^3$, C(O)OR$^4$, (C$_1$-C$_8$)alkyl-N(R$^6$)$_2$, (C$_1$-C$_8$)alkyl-OR$^5$, (C$_1$-C$_8$)alkyl-C(O)OR$^5$, C(O)NHR$^3$, C(S)NHR$^3$, C(O)NR$^3$R$^{3'}$, C(S)NR$^3$R$^{3'}$ or (C$_1$-C$_8$)alkyl-O(CO)R$^5$;

R$^2$ is H, F, benzyl, (C$_1$-C$_8$)alkyl, (C$_2$-C$_8$)alkenyl, or (C$_2$-C$_8$)alkynyl;

R$^3$ and R$^{3'}$ are independently (C$_1$-C$_8$)alkyl, (C$_3$-C$_7$)cycloalkyl, (C$_2$-C$_8$)alkenyl, (C$_2$-C$_8$)alkynyl, benzyl, aryl, (C$_0$-C$_4$)alkyl-(C$_1$-C$_6$)heterocycloalkyl, (C$_0$-C$_4$)alkyl-(C$_2$-C$_5$)heteroaryl, (C$_0$-C$_8$)alkyl-N(R$^6$)$_2$, (C$_1$-C$_8$)alkyl-OR$^5$, (C$_1$-C$_8$)alkyl-C(O)OR$^5$, (C$_1$-C$_8$)alkyl-O(CO)R$^5$, or C(C)OR$^5$;

R$^4$ is (C$_1$-C$_8$)alkyl, (C$_2$-C$_8$)alkenyl, (C$_2$-C$_8$)alkynyl, (C$_1$-C$_4$)alkyl-OR$^5$, benzyl, aryl, (C$_0$-C$_4$)alkyl-(C$_1$-C$_6$)heterocycloalkyl, or (C$_0$-C$_4$)alkyl-(C$_2$-C$_5$)heteroaryl;

R$^5$ is (C$_1$-C$_8$)alkyl, (C$_2$-C$_8$)alkenyl, (C$_2$-C$_8$)alkynyl, benzyl, aryl, or (C$_2$-C$_5$)heteroaryl;

each occurrence of R$^6$ is independently H, (C$_1$-C$_8$)alkyl, (C$_2$-C$_8$)alkenyl, (C$_2$-C$_8$)alkynyl, benzyl, aryl, (C$_2$-C$_5$)heteroaryl, or (C$_0$-C$_8$)alkyl-C(O)O—R$^5$ or the R$^6$ groups can join to form a heterocycloalkyl group;

n is 0 or 1; and

* represents a chiral-carbon center;

or a pharmaceutically acceptable salt, hydrate, solvate, clathrate, enantiomer, diastereomer, racemate, or mixture of stereoisomers thereof. In another embodiment, said immunomodulatory compound is a compound having the structure

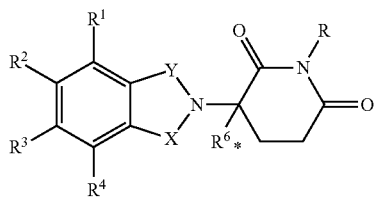

wherein:
one of X and Y is C=O and the other is CH$_2$ or C=O;
R is H or CH$_2$OCOR*;
(i) each of R$^1$, R$^2$, R$^3$, or R$^4$, independently of the others, is halo, alkyl of 1 to 4 carbon atoms, or alkoxy of 1 to 4 carbon atoms or (ii) one of R$^1$, R$^2$, R$^3$, or R$^4$ is nitro or —NHR$^5$ and the remaining of R$^1$, R$^2$, R$^3$, or R$^4$ are hydrogen;
R$^5$ is hydrogen or alkyl of 1 to 8 carbons
R$^6$ hydrogen, alkyl of 1 to 8 carbon atoms, benzo, chloro, or fluoro;
R' is R$^7$—CHR$^{10}$—N(R$^8$R$^9$);
R$^7$ is m-phenylene or p-phenylene or —(C$_n$H$_{2n}$)— in which n has a value of 0 to 4;
each of R$^8$ and R$^9$ taken independently of the other is hydrogen or alkyl of 1 to 8 carbon atoms, or R$^8$ and R$^9$ taken together are tetramethylene, pentamethylene, hexamethylene, or —CH$_2$CH$_2$X$_1$CH$_2$CH$_2$— in which X$_1$ is —O—, —S—, or —NH—;
R$^{10}$ is hydrogen, alkyl of to 8 carbon atoms, or phenyl; and
* represents a chiral-carbon center;
or a pharmaceutically acceptable salt, hydrate, solvate, clathrate, enantiomer, diastereomer, racemate, or mixture of stereoisomers thereof.

In a specific embodiment, expansion of hematopoietic cells is performed in IMDM supplemented with 20% BITS (BSA, recombinant human insulin and transferrin), SCF, Flt-3 ligand, IL-3, and 4-(Amino)-2-(2,6-dioxo(3-piperidyl))-isoindoline-1,3-dione (10 μM in 0.05% DMSD). In a more specific embodiment, about 5×10$^7$ hematopoietic cells, e.g., CD34$^+$ cells, are expanded in the medium to from about 5×10$^{10}$ cells to about 5×10$^{12}$ cells, which are resuspended in 100 mL of IMDM to produce a population of expanded hematopoietic cells. The population of expanded hematopoietic cells is preferably cryopreserved to facilitate shipping.

Production of erythrocytes by the methods and in the media described above, is preferably performed in a bioreactor, e.g., the bioreactor exemplified elsewhere herein.

In various specific embodiments, at least 50%, 55%, 60%, 65%, 70%, 75%, 80%, 85%, 90%, 95%, 97%, 98%, or 99% of the hematopoietic cells are differentiated to erythrocytes and/or polychromatophilic erythrocytes.

In one embodiment, differentiation of hematopoietic cells, e.g., the expanded hematopoietic cells described above, can be accomplished by culturing said cells in contact with an immunomodulatory compound, e.g., a TNF-α inhibitory compound as described above, for a time and in an amount sufficient to cause a detectable increase in the proliferation of the hematopoietic cells over a given time, compared to an equivalent number of hematopoietic cells not contacted with the immunomodulatory compound. See, e.g., U.S. Patent Application Publication No. 2003/0235900, the disclosure of which is incorporated herein by reference in its entirety.

In certain embodiments, the method of expansion and differentiation of the hematopoietic cells, as described herein, comprises maintaining the cell population comprising said hematopoietic cells is maintained at between about 2×10$^4$ and about 2×10$^5$ cells per milliliter during expansion and differentiation. In certain other embodiments, the method of expansion and differentiation of the hematopoietic cells, as described herein, comprises maintaining the cell population comprising said hematopoietic cells is maintained at no more than about 1×10$^5$ cells per milliliter.

Differentiation of the hematopoietic cells into erythrocytes can be assessed by detecting erythrocyte-specific markers, e.g., by flow cytometry. Erythrocyte-specific markers include, but are not limited to, CD36 and glycophorin A. Differentiation can also be assessed by visual inspection of the cells under a microscope. The presence of typical biconcave cells confirms the presence of erythrocytes. The presence of erythrocytes (including reticulocytes) can be confirmed using a stain for deoxyribonucleic acid (DNA), such as Hoechst 33342, TO-PRO®-3. DRAG5 or the like. Nucleated precursors to erythrocytes typically stain positive with a DNA-detecting stain, while erythrocytes and reticulocytes are typically negative. Differentiation of hematopoietic cells to erythrocytes can also be assessed by progressive loss of transferring receptor (CD71) expression and/or laser dye styryl staining during differentiation. Erythrocytes can also be tested for deformability using, e.g., an ektacytometer or diffractometer. See, e.g., Bessis M and Mohandas N, "A Diffractometric Method for the Measurement of Cellular Deformability," Blood Cells 1:307 (1975); Mohandas N. et al., "Analysis of Factors Regulating Erythrocyte Deformability," J. Clin. Invest. 66:563 (1980); Groner W et al., "New Optical Technique for Measuring Erythrocyte Deformability with the Ektacytometer," Clin, Chem. 26:1435 (1980). Fully-differentiated erythrocytes have a mean corpuscular volume (MCV) of about 80 to about 108 fL (femtoliters); mean corpuscular hemoglobin (MCH) of about 17 to about 31 pg, and a mean corpuscular hemoglobin concentration (MCHC) of about 23% to about 36%.

The time for differentiation of hematopoietic cells into erythrocytes can be from about 3 days to about 120 days. In one embodiment, the differentiation time is about 7 days to about 35 days. In another embodiment, the differentiation time is about 14 days to about 28 days.

5.3. Separation of Erythrocytes From Precursors

Erythrocytes produced by the methods described above are preferably separated from hematopoietic cells, and, in certain embodiments, from precursors of erythrocytes. Such separation can be effected, e.g., using antibodies to CD36 and/or glycophorin A. Separation can be achieved by known methods, e.g., antibody-mediated magnetic bead separation, fluorescence-activated cell sorting, passage of the cells across a surface or column comprising antibodies to CD36 and/or glycophorin A, or the like. In another embodiment, erythrocyte separation is achieved by deoxygenating the culture medium comprising the erythrocytes, followed by magnetic separation of deoxygenated erythrocytes from other cells.

Erythrocytes can be continuously separated from a population of cells, e.g., from a second expanded hematopoietic cell population as described above, or can be separated at intervals. In certain embodiments, for example, isolation of erythrocytes is performed, e.g., every 1, 2, 3, 4, 5, 6, 7, 8, 9, 10, 15, 20, 25, 30, 35, 40, 45, 50, 55 or 60 minutes, or every 1, 1.5, 2, 2.5, 3, 3.5, 4, 4.5, 5, 5.5, 6, 6.5, 7.0, 7.5, 8.0, 8.5, 9.0, 9.5, 10.0, 10.5, 11.0, 11.5, 12, 13, 14, 15, 16, 17, 18, 19, 20, 21, 22, 23 or 24 hours, or more, or when one or more culture condition criteria are met, e.g., achievement in the culture of a particular cell density; achievement in the culture of a particular number of cells per milliliter expressing certain erythrocyte markers, e.g., CD36 or glycophorin A; or the like. Separation of erythrocytes from a cell population is preferably performed using a bioreactor, as described below.

5.4 Bioreactor Production of Erythrocytes

In another aspect of the method of producing erythrocytes, hematopoietic cells are expanded and differentiated in a bioreactor in the absence of feeder cells. The bioreactor in which the hematopoietic cells are differentiated can be the same bioreactor in which the hematopoietic cells are expanded, or can be a separate bioreactor. In another embodiment, the bioreactor is constructed to facilitate expansion of the hematopoietic cells entirely in the bioreactor. In another embodiment, the bioreactor is constructed to allow expansion of hematopoietic cells without feeder cells.

In another embodiment, the bioreactor is constructed to allow continuous flow of cells in media, enabling the continuous separation of differentiated erythrocytes from remaining cells in the bioreactor. The continuous flow and cell separation allows for the bioreactor to be constructed in a substantially smaller volume than would bioreactors using batch methods of producing erythrocytes. In another embodiment, the bioreactor is constructed to allow periodic, e.g., non-continuous flow of cells in media, enabling the periodic separation of differentiated erythrocytes from remaining cells in the bioreactor. The periodic flow and cell separation preferably allows for the bioreactor to be constructed in a substantially smaller volume than would bioreactors using batch methods of producing erythrocytes. In specific embodiments, isolation of erythrocytes is performed, e.g., every 1, 2, 3, 4, 5, 6, 7, 8, 9, 10, 15, 20, 25, 30, 35, 40, 45, 50, 55 or 60 minutes, or every 1, 1.5, 2, 2.5, 3, 3.5, 4, 4.5, 5, 5.5, 6, 6.5, 7.0, 7.5, 8.0, 8.5, 9.0, 9.5, 10.0, 10.5, 11.0, 11.5, 12, 13, 14, 15, 16, 17, 18, 19, 20, 21, 22, 23 or 24 hours, or more. In another specific embodiment, isolation of erythrocytes is performed periodically when one or more culture condition criteria are met e.g., achievement in the culture of a particular cell density; achievement in the culture of a particular number of cells per milliliter expressing certain erythrocyte markers, e.g., CD36 or glycophorin A; or the like.

In certain embodiments, the bioreactor is disposable.

In one embodiment, the bioreactor comprises a culturing element and a cell separation element. In another embodiment, the bioreactor comprises a medium gas provision element. In another embodiment, the bioreactor comprises a cell factor element comprising one or more bioactive compounds. In another embodiment, the elements of the bioreactor are modular; e.g., separable from each other and/or independently usable. In one embodiment, the capacity of the bioreactor is about 100 mL, 200 mL, 300 mL, 400 mL, 500 mL, 600 mL, 700 mL, 800 mL, or about 900 mL, or about 1, 2, 3, 4, 5, 6, 7, 8, 9, 10, 12, 14, 16, 18, 20, 25, 30, 35, 40, 45 or 50 liters. In another embodiment, the bioreactor, including all components, occupies about 47 cubic feet or less. In another embodiment, the bioreactor is capable of culturing up to about $10^{10}$, $10^{11}$, or about $10^{12}$ cells, e.g., hematopoietic cells.

In one embodiment, the culturing element comprises a compartment able to receive culture medium, e.g., culture medium comprising hematopoietic cells. The culturing element comprises a port that allows for the introduction of media and/or hematopoietic cells for culture. Such a port can be any art-acceptable port for such devices, e.g., a Luer-lock seal port. The culturing element also comprises one or more ports for the passage of media to the cell separation element. The culturing element optionally further comprises a port for the introduction of bioactive compounds into the interior of the culturing element, e.g., a port that facilitates connection of the cell factor element to the culturing element. In a specific embodiment, hematopoietic cells, including differentiating hematopoietic cells, in the culturing element are continuously circulated in medium to a cell separation element (see below) to isolate erythrocytes and/or polychromatophilic erythrocytes and/or other erythrocyte precursors.

The culturing element, in a specific embodiment, comprises a plurality of interior surfaces or structures, e.g., tubes, cylinders, hollow fibers, a porous substrate, or the like. The surfaces can be constructed of any material suitable for the culture of cells, e.g., tissue culture plastic, flexible pharmaceutical grade plastic, hydroxyapatite, polylactic acid (PLA), polyglycolic acid copolymer (PLGA), polyurethane, polyhydroxyethyl methacrylate, or the like. Hollow fibers typically range from about 100 μm to about 1000 μm in diameter, and typically comprise pores that allow passage of molecules no more than about 5 kDa, 10 kDa, 15 kDa, 20 kDa, 30 kDa, 40 kDa, 50 kDa, 60 kDa, 70 kDa, 80 kDa, 90 kDa, 100 kDa, 125 kDa, 150 kDa, 175 kDa, 200 kDa, 150 kDa, 300 kDa, 350 kDa, 400 kDa, 450 or 500 kDa.

The cell separation element comprises at least one port for receiving medium, comprising cells, from the culturing element. The cell separation element comprises one or more components that facilitate or enable the separation of at least one type of cell, e.g., erythrocytes, from cells in medium from the culture element. Such separation can be effected, e.g., using antibodies to CD36 and/or glycophorin A. Separation can be achieved by known methods, e.g., antibody-mediated magnetic bead separation, fluorescence-activated cell sorting, passage of the cells across a surface or column comprising antibodies to CD36 and/or glycophorin A, or the like. Separation can also be achieved based on cell size or cell density. In a specific embodiment, the cell separation element is connected to the cell culturing element, and medium comprising hematopoietic cells, differentiating hematopoietic cells and erythrocytes is continually passed through the cell separation element so as to continually remove cells, e.g., erythrocytes from the medium.

In another embodiment, erythrocyte separation is achieved by deoxygenating culture medium comprising the erythrocytes, followed by magnetic attraction of deoxygenated erythrocytes, e.g., to a surface or other point of collection.

In another embodiment, the bioreactor comprises a cell separation element. The cell separation element can comprise one or more components that enable the separation of one or more non-erythrocytic cells (e.g., undifferentiated, or non-terminally differentiated hematopoietic cells) from erythrocytes in the medium. In certain embodiments, the cell separation element is able to calculate an approximate number of erythrocytes generated, or is able to alert a user that a sufficient number of erythrocytes has been generated to constitute a unit, according to preset user parameters.

The bioreactor, in another embodiment, further comprises a gas provision element that provides appropriate gases to the culture environment, e.g., contacts the culture medium with a mixture of 80% air, 15% $O_2$ and 5% $CO_2$, 5% $CO_2$ in air, or the like. In another embodiment the bioreactor comprises a temperature element that maintains the medium, the bioreactor, or both at a substantially constant temperature, e.g., about 35° C. to about 39° C., or about 37° C. In another embodiment, the bioreactor comprises a pH monitoring element that maintains the medium at a constant pH, e.g., about pH 7.2 to about pH 7.6, or about pH 7.4, In specific embodiments, the temperature element and/or pH monitoring element comprises a warning that activates when temperature and/or pH exceed or fall below set parameters. In other specific embodiments, the temperature element and/or pH monitoring element are capable of correcting out-of-range temperature and/or pH.

In a specific embodiment, the bioreactor comprises a cell separation element and a gas provision element that provides gases to the culture environment, whereby the gas provision element enables the partial or complete deoxygenation of erythrocytes, enabling erythrocyte separation based on the magnetic properties of the hemoglobin contained therein. In a more specific aspect, the bioreactor comprises an element that allows for the regular, or iterative, deoxygenation of erythrocytes produced in the bioreactor, to facilitate magnetic collection of the erythrocytes.

In another embodiment, the function of the bioreactor is automated, e.g., controlled by a computer. The computer can be, for example, a desktop personal computer, a laptop computer, a Handspring, PALM® or similar handheld device; a minicomputer, mainframe computer, or the like.

5.5. Erythrocyte Units Produced From Hematopoietic Cells

Erythrocyte units produced according to the methods detailed above can comprise erythrocytes in any useful number or combination of genetic backgrounds.

In various embodiments, erythrocyte units produced by the methods provided herein comprise at least about, at most about, or about $1 \times 10^8$, $5 \times 10^8$, $1 \times 10^9$, $5 \times 10^9$, $1 \times 10^{10}$, $5 \times 10^{10}$, $1 \times 10^{11}$, $5 \times 10^{11}$ or $1 \times 10^{12}$ erythrocytes. In various other embodiments, the erythrocyte units comprise at least 10%, 15%, 20%, 25%, 30%, 40%, 50%, 60%, 70%, 80%, 90%, 95%, 98% or 99% completely-differentiated erythrocytes. In various other embodiments, the erythrocyte units comprise less than 60%, 50%, 40%, 30%, 20%, 10%, 5%, 2% or 1% erythrocyte precursors of any kind. In certain embodiments, the erythrocyte units produced by the methods described herein comprise less than about 60%, about 50%, about 40%, about 30%, about 20%, about 19%, about 18%, about 17%, about 16%, about 15%, about 14%, about 14%, about 12%, about 11%, about 10%, about 9%, about 8%, about 7%, about 6% or about 5% reticulocytes, or other non-erythrocytic hematopoietic cells. In another embodiment, the unit comprises erythrocytes from hematopoietic cells from a single individual. In another embodiment, the unit comprises erythrocytes differentiated from hematopoietic cells from a plurality of individuals. In another embodiment, the unit comprises erythrocytes from hematopoietic cells from matched human placental perfusate and cord blood. In another embodiment, substantially all (e.g., greater than 99%) of the erythrocytes in a unit of erythrocytes are type O. In another embodiment, substantially all (e.g., greater than 99%) of the erythrocytes in a unit of erythrocytes are type A. In another embodiment, substantially all (e.g., greater than 99%) of the erythrocytes in a unit of erythrocytes are type B. In another embodiment, substantially all (e.g., greater than 99%) of the erythrocytes in a unit of erythrocytes are type AB. In another embodiment, substantially all (e.g., greater than 99%) of the erythrocytes in a unit of erythrocytes are Rh positive. In another embodiment, substantially all (e.g., greater than 99%) of the erythrocytes in a unit of erythrocytes are Rh negative.

Naturally-occurring erythrocytes possess certain characteristics that allow the flow of blood through capillaries. For example, erythrocytes in the aggregate produce non-Newtonian flow behavior, e.g., the viscosity of blood is highly dependent upon shear rates. Normal erythrocytes are deformable and able to build up aggregates/rouleaux. The deformability of erythrocytes appears to be related to their lifespan in the blood, about 100-120 days; removal of erythrocytes from the blood appears to be related to loss of deformability. Normal aggregability of erythrocytes facilitates the cells' flow through the capillaries, while abnormally increased or decreased aggregability decreases flow. Thus, in preferred embodiments, units of erythrocytes produced by the methods disclosed herein are assayed as a part of quality control, e.g., for one or more characteristics of naturally-occurring erythrocytes. In certain embodiments, samples of erythrocytes produced by the methods disclosed herein are suspended in natural or artificial plasma and tested for one or more of viscosity, viscoelasticity, relaxation time, deformability, aggregability, blood/erythrocyte suspension yield stress, and mechanical fragility, using normal blood or normal erythrocytes as a control or comparator. In certain other embodiments, samples of erythrocytes produced as described herein are assayed for oxygen carrying capacity and oxygen release capacity, using normal blood or an equivalent number of naturally-occurring erythrocytes as a control.

6. EXAMPLES

6.1. Example 1: Characterization of CD34+ Cells from Human Placental Perfusate (HPP) and Umbilical Cord Blood (UCB)

Umbilical cord blood (UCB) was removed from postpartum placentas under informed consent. The exsanguinated placentas were then perfused to generate HPP, as described in U.S. Pat. No. 7,045,148, the disclosure of which is incorporated herein by reference in its entirety. After removal of red blood cells (RBCs) the total nucleated cells (TNCs) were collected and frozen. This method typically resulted in the collection of about 1-2.5×10$^9$ TNCs, compared to around 500 million TNC isolated from UCB.

Flow cytometric analysis of the TNC isolated from exsanguinated placentas indicates a high percentage of CD34$^+$ cell population as compared to conventional umbilical cord blood (UCB) generated cellular product. TNC from HPP, collected as above, contains about 2% to 6% CD34$^+$ cells, compared to about 0.3% to 1% of the TNC in UCB.

The flow cytometric analysis of the TNC isolated from HPP indicates that a high percentage of the CD34$^+$ cell population is CD45$^-$ (FIG. 1).

CD34$^+$ cells from HPP were plated in a colony-forming unit assay, and the ratio (%) of the burst forming unit-erythroid (BFU-E) to the colony forming unit-erythroid (CFU-E) was determined, as well as the number of colony-forming unit-granulocyte, macrophage (CFU-GM) and the number of colony-forming unit-granulocyte, erythrocyte, monocyte (CFU-GEMM) (Table 1). The elonogenicity was also assessed (Table 1).

TABLE 1

| Sample | Cell Purity | BFU-E/CFU-E | CFU-GM | CFU-GEMM | Clonogenicity |
|---|---|---|---|---|---|
| Donor 1 | 88% | 50.1% | 49.5% | 0.4% | 23.1% |
| Donor 2 | 92% | 54.1% | 44.1% | 1.7% | 26.1% |
| Donor 3 | 94% | 32.7% | 60.6% | 6.7% | 19.7% |

The colony-forming unit assay was performed according to the manufacturer's protocol (StemCell Technologies, Inc.). In brief, CD34$^+$ cell suspensions were placed into a methylcellulose medium supplemented with stem cell factor (SCF), granulocyte colony-stimulating factor (G-CSF), granulocyte-macrophage colony-stimulating factor (GM-CSF), interleukin 3 (IL-3), interleukin 6 (IL-6) and erythropoietin (Epo) at 100 cells/plate, 300 cells/plate and 1000 cells/plate. For each cell density, a triplicate assay was performed followed by incubation for 2 to 3 weeks. Colony evaluation and enumeration were performed using light microscopy.

In a separate experiment, the ratio (BFU-E)/(CFU-E) for CD34$^+$ cells from HPP and UCB was 46% and 30%, respectively (based on the average value for three donors).

These results suggest that HPP-derived cells contain a higher number of CD34$^+$ cells with increased erythrogenic activity relative to UCB-derived stem cells.

6-2. Example 2: Recovery of Hematopoietic Stem Cells (HSCs)

HPP and UCB cells were generally purified as described in Example 1 using either Ficoll, hetastarch or ammonium chloride to obtain total nucleated cells (TNCs). TNCs were then used in a positive selection procedure to isolate CD34$^+$ cells using anti-CD34 beads and RoboSep following the protocol provided by the manufacturer (StemCell Technologies, Inc.) In this experiment, CD34$^+$ cells were isolated with greater than 90% purity (FIG. 2). Alternatively, EASY-SEP® Human Progenitor Cell Enrichment Kit (StemCell Technologies, Inc.) was used in a negative selection procedure to deplete the lineage committed cells by using Human Progenitor Cell Enrichment Cocktail with monoclonal antibodies to the following human cell surface antigens: CD2, CD3, CD11b, CD11c, CD14, CD16, CD19, CD24, CD56, CD66b, Glycophorin A. Using the negative selection process, 90% CD34$^+$ cells were recovered from the raw materials; the cell composition of the recovered HSCs is summarized in Table 2.

A colony-forming unit assay of the isolated CD34$^+$ cells showed that the colony forming frequency of negative selection HSCs is comparable to positive selection HSCs and the BFU-E forming frequency of negative selection HSCs is higher than that of positive selection HSCs.

TABLE 2

Cell composition of enriched HSCs. Standard deviation was calculated for population means for 3 donors.

|  | Mean % | Stdev |
|---|---|---|
| Lin-CD34$^+$ | 75.1 | 6.2 |
| Lin-CD34$^-$CD38$^-$ | 9.8 | 2.4 |
| Lin-CD34$^-$CD133$^+$ | 0.9 | 0.2 |
| Lin-CD34$^-$CD117$^+$ | 7.2 | 0.5 |

6.3. Example 3: Expansion of CD34$^+$ Hematopoietic Cell Populations

The CD34$^+$ cell content of human umbilical cord blood (UCB) units is often not sufficient to provide for hematopoietic cell transplants in adult patients. Ex-vivo expansion of CD34$^+$ cells from UCB is one approach to overcome this CD34$^+$ cell dose limitation. This Example demonstrates expansion of CD34$^+$ cells using a specific immunomodulatory drug, 4-(Amino)-2-(2,6-dioxo(3-piperidyl))-isoidoline-1,3-dione (referred to in this Example as pomalidomide).

The ability of pomalidomide to enhance the expansion of human UCB derived CD34$^+$ cells in a short-term serum-free, cytokine supplemented culture system was evaluated. CD34$^+$ progenitor cells were enriched from cryopreserved UCB units to >90% purity and seeded (104 CD34$^+$ cells) in 1 mL of growth medium, which consists of IMDM plus serum substitute BIT (BSA, recombinant human insulin and transferrin, 20%), in the presence of SCF (50 ng/mL), Flt-3 ligand (50 ng/mL), and IL-3 (10 ng/mL). Pomalidomide, dissolved in DMSO, was supplemented at 2.7 µg/mL. The culture was incubated at 37° C., 5% CO$_2$ for 12 days, with fresh medium added at day 7. Pomalidomide-free cultures with or without DMSO (0.05% v/v) were used as controls.

In one experiment, pomalidomide supplementation resulted in significantly higher CD34$^+$ expression in the expanded population without impacting total nucleated cell expansion (200-350 fold). CD34$^+$ phenotype in the pomalidomide-expanded population was 40-60%, compared with 10-30% in the control. Additionally, pomalidomide appeared to down-regulate CD38 expression on cultured cells. Pomalidomide-expanded CD34$^+$ cells were primarily CD38 negative (95%) and expressed lower levels of CD133 (15% vs. 40% in the control). Pomalidomide-expanded CD34$^+$ cells demonstrated substantial improvement in cumulative colony forming units relative to expanded controls. In another, similar, experiment, pomalidomide supplementation was confirmed to result in significantly higher CD34$^+$ expression in the expanded population without impacting total nucleated cell expansion (200-350 fold). CD34$^+$ phenotype in the pomalidomide-expanded population was 40-60%, compared with 10-30% in the control (FIG. 3). Additionally, pomalidomide appeared to down-regulate CD38 expression on cultured cells. Pomalidomide-expanded CD34+ cells were primarily CD38 negative (97%) and expressed lower levels of CD133 (11.5% vs. 32.3% in the control). Pomalidomide-expanded CD34+ cells demonstrated substantial improvement in cumulative colony forming units relative to expanded controls.

The pomalidomide-based CD34+ expansion process was scaled up to demonstrate the production of a larger number of CD34+ cells. CD34+ cells were seeded in $10^4$/mL pomalidomide-supplemented medium in a flexible, gas-permeable fluorocarbon culture bag (American Fluoroseal). After 7 days of incubation, the culture was centrifuged and exchanged with fresh pomalidomide-supplemented medium at three times the initial volume. By day 12, TNC and CD34+ expansion were 350 (range: 250-700) and 200 (range: 100-450) fold, respectively (FIG. 4). Viability was 86% (range: 80-90%) by trypan blue. A total of 20 million CD34+ cells were harvested. These results demonstrate that pomalidomide significantly enhanced the ex-vivo expansion of placental derived CD34+ progenitors and that the process can produce a sufficient amount of CD34+ cells for erythrocytic differentiation.

6.4. Example 4: Feeder Cell-Free Expansion and Differentiation of Hematopoietic Stem Cells into Erythrocytes This Example demonstrates continuous expansion and differentiation of hematopoietic stem cells or precursor cells into erythrocytes using medium comprising SCF, IL-3 and Epo, and lacking Fms-like tyrosine kinase 3 ligand (FLT-3L), thrombopoietin (Tpo) and IL-11.

CD34+ cord blood cells were cultured in the following medium formulations and aliquots of cells were taken for assessment of cell count, cell viability and characterization of erythrocytic differentiation.

C medium: IMDM medium supplemented with 1% deionized BSA (Cat# A4919. Sigma), 120 µg/mL iron-saturated human transferring (Cat# T0665. Sigma), 900 ng/mL ferrous sulfate (Cat# F8048, Sigma), 90 ng/mL ferric nitrate (Cat# F8508, Sigma) and 10 µg/mL insulin (Cat #10908, Sigma), 100 ng/ml SCF, 1 µM hydrocortisone (Cat# H0135, Sigma), 5 ng/mL IL-3 and 3 IU/ml Epo (Cat #287-TC, R&D Systems).

E1 medium: serum-free medium (STEMSPAN®, Cat #09650, Stem Cell Technologies, Vancouver, Canada) supplemented with 2 IU/mL Epo, 1 µM synthetic glucocorticoid dexamethasone (Dex, Cat# D4902, Sigma, St Louis, Mo.), 40 ng/mL insulin-like growth factor 1 (IGF-1, Cat#291-G1-250, R&D Systems, Minneapolis, Minn.), 100 ng/mL SCF, and 40 µg/mL lipids (cholesterol-rich lipid mix; Cat# C7305-1G, Sigma. St Louis. Mo.).

E2 medium: serum-free medium STEMSPAN® was supplemented with 2 IU/mL Epo, 1 µM hydrocortisone, 40 ng/mL IGF-1, 100 ng/mL SCF, and 40 µg/mL lipids.

E3 medium: serum-free medium STEMSPAN® was supplemented with 3 IU/mL Epo, 1 µM Dex, 40 ng/mL IGF-1, 100 ng/mL SCF, 5 ng/mL IL-3 and 40 µg/mL lipids.

E4 medium: serum-free medium STEMSPAN® was supplemented with 3 IU/mL Epo, 1 µM hydrocortisone, 40 ng/mL IGF-1, 100 ng/mL SCF, 5 ng/mL IL-3 and 40 µg/mL lipids.

FIG. 5 shows the 21-day cell expansion in medium formulations C and E1. In summary, levels of cell expansion were up to $2.5 \times 10^5$ fold with a mean of $7.0 \times 10^4$ fold (n=13), levels of CD235A+ cells up to 37.6%, and levels of enucleation up to 28.1% in C medium; levels of cell expansion were up to $2.6 \times 10^5$ fold with a mean of $1.0 \times 10^5$ fold (n=10), levels of CD235A+ cells up to 92.9%, and levels of enucleation up to 48.2% in E medium. Cells expanded in these media all exhibited greater than 90% viability. Cells expanded in E1 medium exhibited the highest erythroid differentiation represented by the highest proportion of CD235A+ cells and enucleated cells.

Cell expansion in 3 more medium formulations E2, E3 and E4 was examined (FIG. 6). When the cultures reached day 21 and further to day 28, cells in E1 medium and E2 medium showed a growth plateau, while high cell proliferation was seen in E3 medium and E4 medium. Cells cultured for 21 days were subjected to immunophenotypic Characterization, FACS-based analyses of enucleation (TO-PRO-3. Cat# T3605, Invitrogen) and production of fetal hemoglobin (HbF-PE, Cat #560041, BD Biosciences) and adult hemoglobin (HbA-FITC, Cat# sc-21757, Santa Cruz)) (Table 3).

Table 3A, 3B. Characterization of day 21-cultured cells. (A) Immunophenotypic characterization; (B) Characterization of enucleation, HbF and HbA. Standard deviation was calculated for population means for 3 donors.

TABLE 3A

| | % CD34+ | | % CD38+ | | % CD117+ | | % CD133+ | | % CD71+ | | % CD36+ | | % CD235a | |
|---|---|---|---|---|---|---|---|---|---|---|---|---|---|---|
| | Mean | STDEV | Mean | STDEV | Mean | STDEV | Mean | STDEV | Mean | STDEV | Mean | STDEV | Mean | STDEV |
| E1 | 0.8 | 0.7 | 1.1 | 0.8 | 14.6 | 5.8 | 0.9 | 0.4 | 95.4 | 4.5 | 98.1 | 0.6 | 87.6 | 3.4 |
| E2 | 0.4 | 0.2 | 0.7 | 0.1 | 14.4 | 6.3 | 0.8 | 0.2 | 95.5 | 1.7 | 97.9 | 0.4 | 85.6 | 3.1 |
| E3 | 0.5 | 0.2 | 0.8 | 0.4 | 16.2 | 6.9 | 0.9 | 0.4 | 97.1 | 1.3 | 97.5 | 1.0 | 78.7 | 2.6 |
| E4 | 0.2 | 0.1 | 0.5 | 0.1 | 17.7 | 8.2 | 0.7 | 0.3 | 96.5 | 1.4 | 96.3 | 1.0 | 70.8 | 2.9 |

TABLE 3B

| | % Enucleation | | % HbF | | % HbA | |
|---|---|---|---|---|---|---|
| | Mean | STDEV | Mean | STDEV | Mean | STDEV |
| E1 | 47.67 | 5.17 | 90.10 | 2.33 | 39.82 | 17.34 |
| E2 | 42.93 | 4.63 | 90.07 | 1.15 | 34.33 | 16.61 |
| E3 | 41.97 | 6.12 | 91.90 | 0.60 | 37.36 | 16.42 |
| E4 | 33.30 | 7.50 | 86.77 | 2.04 | 27.07 | 14.10 |

Additionally, FACS analysis of HSCs markers (including CD34, CD117, and CD133) and erythocytic markers (including CD235A, CD36, and CD71) was performed using aliquots of cultures at serial time intervals of cultures in E3 medium. A commitment to the erythroid lineage was evident by day 7, as the expression of immature progenitor markers diminished for the CD34+ cell population, as wall as for the CD117+ and CD133+ cell populations, while 56% of the expanded cells were CD235A+. The subsequent terminal differentiation was demonstrated by continuously increased expression of CD235A through days 7, 14, 21 and 28, increased presence of the enucleated cells, particularly between days 14 and 21, and increased production of both HbF and HbA through days 7, 14, 21 and 28. At day 21 of cultures, nearly 50% of the expanded cells were enucleated, 80% were HbF+, and 30% were HbA+.

Cells isolated by positive selection procedure and negative selection procedure were examined for expandability and differentiation in B medium (Table 4). Positively selected cells yielded average fold expansion of $2.2 \times 10^4 \pm 2.0 \times 10^4$; proportion of CD235+ cells was 32.2%±14.8%; proportion of enucleated cells was 23.9%±7%. Negatively selected cells yielded average fold expansion of $4.0 \times 10^4 \pm 3.8 \times 10^4$; proportion of CD235+ cells was 40.9%±11.0%; proportion of enucleated cells was 19.1%±4.8%. Based on the above results, no significant difference of fold expansion and differentiation was observed for cells derived from the positive and negative cell selection procedures.

TABLE 4

Evaluation of cells derived from positive and negative cell isolation procedures. Standard deviation was calculated for population means for 3 donors.

|  | Positive Selection | | Negative Selection | |
| --- | --- | --- | --- | --- |
|  | Average | STDEV | Average | STDEV |
| Fold Expansion | 2.20E+04 | 2.00E+04 | 4.00E+04 | 3.80E+04 |
| % CD235+ | 32.2 | 14.8 | 40.9 | 11 |
| % Enucleation | 23.9 | 7 | 19.1 | 4.8 |

6.5. Example 5: Effects of Cell Density on HSCs Expansion

HSCs were obtained from cord blood as described in Example 1. HSC cultivation was then initiated by culturing the enriched CB-derived HSCs E3 medium as described in Example 4. Every 3 to 4 days, the cultured cells were subjected to cell counting and characterizations. The cultured cells were then diluted to desired densities using fresh medium.

Six cell densities were examined for effects on cell proliferation throughout 26-day cultivation in E3 medium (FIG. 7 & Table 5). Cells maintained at a range of 2 to $5 \times 10^4$ cells/mL showed the highest proliferation. Cells kept at $>5 \times 10^5$ cells/mL showed slower expansion.

6.6. Example 6: CD34+ Cells Derived from Placenta and Bone Marrow in Expansion and Differentiation into Erythrocytes In this Example, a comparison of cell expansion and differentiation potential between CB and bone marrow (BM) CD34+ cells in E3 medium was performed. Cells derived from 3 units of BM or CB as described in Example 1 were used in the evaluation studies. CB CD34+ cells showed a higher proliferation potential compared with BM CD34+ cells (FIG. 8), while differentiation potential was comparable (Table 6A). The proportions of cells containing adult hemoglobin (HbA) and fetal hemoglobin (HbF) (as compared to the total number of cells containing hemoglobin) are shown in Table 6B.

TABLE 6A

|  |  | Day 21 fold expansion | % CD235A+ |
| --- | --- | --- | --- |
| BM CD34+ | Average | 8.09E+05 | 87.40 |
|  | STDEV | 1.45E+05 | 3.08 |
| CB CD34+ | Average | 1.01E+06 | 73.50 |
|  | STDEV | 8.06E+04 | 3.70 |

TABLE 6B

|  |  | HbA (%) | HbF (%) |
| --- | --- | --- | --- |
| BM CD34+ | Average | 73.83 | 57.38 |
|  | STDEV | 2.10 | 10.64 |
| CB CD34+ | Average | 22.99 | 88.70 |
|  | STDEV | 4.72 | 3.29 |

6.7. Example 7: Long Term Expansion and Differentiation into Erythrocytes

In this experiment, long term cell expansion was performed using E3 medium (see Example 4, above) and CD34+ cells derived from a single donor and mixed donors. Sustained cell growth up to 63 days with high RBC maturation efficiency was demonstrated (FIG. 9). At day 63, $1 \times 10^9$- and $1.8 \times 10^4$-fold expansion for the mixed donor and single donor cells, respectively, were observed, and 77% CD235A+ and 56% enucleation were achieved for the single donor (Table 7).

TABLE 5

Effects of cell density on cell expansion

|  | Density | D0 | D9 | D12 | D14 | D16 | D19 | D21 | D23 | D26 |
| --- | --- | --- | --- | --- | --- | --- | --- | --- | --- | --- |
| 1 | $2 \times 10^4$ | 1.00E+00 | 4.22E+01 | 7.73E+02 | 1.09E+04 | 6.96E+04 | 9.27E+05 | 5.78E+06 | 4.35E+07 | 2.80E+08 |
| 2 | $5 \times 10^4$ | 1.00E+00 | 2.92E+01 | 7.29E+02 | 5.81E+03 | 6.09E+04 | 7.51E+05 | 3.51E+06 | 9.74E+07 | 4.84E+08 |
| 3 | $1 \times 10^5$ | 1.00E+00 | 3.51E+01 | 5.03E+02 | 3.33E+03 | 3.15E+04 | 4.84E+05 | 1.76E+06 | 5.14E+07 | 1.70E+08 |
| 4 | $2 \times 10^5$ | 1.00E+00 | 2.79E+01 | 3.43E+02 | 1.82E+03 | 1.46E+04 | 2.14E+05 | 8.03E+06 | 1.76E+07 | 7.48E+07 |
| 5 | $5 \times 10^5$ | 1.00E+00 | 3.19E+01 | 1.59E+02 | 4.35E+02 | 2.11E+03 | 1.71E+04 | 5.60E+04 | 6.49E+05 | 2.71E+06 |
| 6 | $1 \times 10^6$ | 1.00E+00 | 2.97E+01 | 8.74E+01 | 1.70E+02 | 6.15E+02 | 2.54E+03 | 5.71E+03 | 4.14E+04 | 1.27E+05 |

TABLE 7

FACS analysis of CD235A+ cells and enucleation of
the long term cultures derived from a single donor.

|  | Day 21 | Day 28 | Day 35 | Day 42 | Day 49 | Day 56 | Day 63 |
|---|---|---|---|---|---|---|---|
| % CD235A | 65.3 | 78.6 | 74.8 | 63 | 55.4 | 61.4 | 70.4 |
| % Enucleation | 39.3 | 41.3 | 40.3 | 47.3 | 46.5 | 53.9 | 51.9 |

FIG. 10 shows the ELISA analysis of HbF and HbA production in the long term cultures derived from a single donor as compared to those in peripheral blood (PB) RBCs. In this experiment, $2\times10^5$ cells collected at the indicated time points were washed with PBS and spun at 2500×g for 10 min. Cell pellets were lysed with 100□ M-PER Mammalian Protein Extraction Reagent (Cat #78501, Thermo Scientific), and the mixture was mixed gently for 10 minutes followed by centrifugation at 14,000×g for 15 minutes. The supernatant was then transferred to a new tube for hemoglobin analysis using the ELISA kits: human hemoglobin ELISA quantitation set (Cat# E80-135) and human fetal hemoglobin ELISA quantitation set (Cat# E80-136). While 1 million PB erythrocytes produced 245 ng HbA, cultured cells produced 1.3 μg HbA starting at day 14 of cultivation.

Table 8 shows quantitative real-time PCR (qRT-PCR) analysis of expression of several genes in long time cultures derived from a single donor. Aliquots of cells were taken at various time points and subjected to qRT-PCR analysis using the 79001HT Fast Real-Time PCR System (Applied Biosystems) and TaqMan® Gene Expression Assays of EKLF (Applied Biosystems, Cat# Hs00610592_m1), GATA1 (Applied Biosystems, Cat# Hs00231112_m1), GATA2, HBβ (Applied Biosystems, Cat# Hs00758889_st), HBγ, (Applied Biosystems, Cat# Hs00361131$_{13}$g1), LMO2 (Applied Biosystems, Cat# Hs00277106_m1) and ZFPM1 (Applied Biosystems, Cat# Hs00419119_m1). The qRT-PCR analysis results showed the sustained growth and differentiation into erythrocytes were correlated with increased expression of HBβ, HBγ, and several transcription factors that are crucial for erythrocytic differentiation, including EKLF, GATA1, LMO2 and ZFPM1.

6.8. Example 8: Optimization of E3 Medium

In this Example, E3 medium was further optimized to improve HSC expansion and differentiation into erythrocytes using a 3-level (3 factors: SCF, Epo and IL-3) full factorial experiment design (FIG. 11). CD34+ cells were obtained as described in FIG. 1 and E3 medium was supplemented with SCF, IL-3 and EPO shown in Table 9. Cell count, viability, proportion of CD235A+ cells and proportion of enucleated cells were examined at the time points indicated in Table 10. One formulation (#7, 65 ng/mL SCF, 7 ng/mL IL-3 and 3 IU/mL Epo) showed an increased proportion of CD235A+ cells and increased enucleation as compared to the E3 medium formulation.

TABLE 9

Design of Experiment for E3 medium optimization

| | Experimental Design | | |
|---|---|---|---|
| Condition# | SCF (ng/mL) | IL-3 (ng/mL) | EPO (IU/mL) |
| 1 | 65 | 7 | 1 |
| 2 | 65 | 3 | 1 |
| 3 | 135 | 3 | 1 |
| 4 | 135 | 7 | 1 |
| 5 | 100 | 5 | 2 |
| 6 | 65 | 3 | 3 |
| 7 | 65 | 7 | 3 |
| 8 | 135 | 3 | 3 |
| 9 | 135 | 7 | 3 |
| E3 | 100 | 5 | 3 |

TABLE 8 qRT-PCR analysis of long term cultures derived from a single donor. (A) Fold change of gene expression;
(B) Gene description. Standard deviation was calculated for means of fold change for 2 replicates.

Table 8A

| | EKLF | | GATA1 | | GATA2 | | HBβ | | HBγ | | LMO2 | | ZFPM1 | |
|---|---|---|---|---|---|---|---|---|---|---|---|---|---|---|
| | Mean | STDEV | Mean | STDEV | Mean | STDEV | Mean | STDEV | Mean | STDEV | Mean | STDEV | Mean | STDEV |
| Day0 | 1.0 | 0.2 | 1.0 | 0.1 | 1.0 | 0.1 | 1.0 | 0.3 | 1.0 | 0.1 | 1.0 | 0.3 | 1.0 | 0.2 |
| Day7 | 17.6 | 0.2 | 2.4 | 0.0 | 0.3 | 0.0 | 4.8 | 0.1 | 1.7 | 0.0 | 1.0 | 0.1 | 1.0 | 0.1 |
| Day14 | 45.5 | 0.4 | 6.2 | 0.7 | 1.0 | 0.0 | 23.9 | 1.4 | 19.8 | 0.1 | 2.7 | 0.2 | 2.4 | 0.1 |
| Day21 | 51.5 | 3.1 | 6.4 | 0.1 | 0.9 | 0.1 | 41.5 | 3.3 | 21.6 | 1.0 | 2.3 | 0.3 | 2.2 | 0.0 |
| Day28 | 64.5 | 14.1 | 6.9 | 0.2 | 1.2 | 0.0 | 46.2 | 1.2 | 26.0 | 1.8 | 3.6 | 0.2 | 3.3 | 0.6 |
| Day35 | 38.5 | 1.6 | 10.1 | 1.0 | 1.5 | 0.2 | 16.2 | 0.4 | 16.0 | 0.4 | 2.9 | 0.2 | 6.0 | 1.6 |
| Day42 | 31.4 | 1.9 | 5.9 | 0.0 | 0.8 | 0.0 | 8.2 | 0.1 | 12.2 | 0.2 | 1.7 | 0.0 | 1.5 | 0.2 |
| Day49 | 38.3 | 2.5 | 5.1 | 0.1 | 0.7 | 0.1 | 4.5 | 1.0 | 11.4 | 0.2 | 1.3 | 0.1 | 1.7 | 0.4 |
| Day56 | 46.0 | 2.5 | 5.8 | 0.1 | 0.6 | 0.0 | 6.2 | 0.5 | 25.0 | 1.8 | 1.5 | 0.1 | 2.4 | 0.1 |
| Day63 | 67.4 | 2.1 | 9.2 | 0.2 | 1.2 | 0.0 | 12.1 | 0.8 | 32.0 | 1.4 | 3.7 | 0.2 | 2.8 | 0.0 |

Table 8B

| Symbol | Description |
|---|---|
| EKLF | Kruppel-like factor 1 (erythroid) |
| GATA1 | GATA binding protein 1 (globin transcription factor 1) |
| GATA2 | GATA binding protein 2 |
| HBβ | Hemoglobin, beta |
| HBγ | Hemoglobin, gamma |
| LMO2 | LIM domain only 2 (rhombotin-like I) |
| ZFPM1 | zinc finger protein, multitype 1 |

TABLE 10

Summary of E3 medium optimization at Day 21.

| Condition# | Means | | | STDEV | | |
|---|---|---|---|---|---|---|
| | fold expansion | % CD235A | % Enucleation | fold expansion | % CD235A | % Enucleation |
| 1 | 6.5E+05 | 74.7 | 13.2 | 4.1E+04 | 21.2 | 7.0 |
| 2 | 6.1E+05 | 71.2 | 15.2 | 1.1E+05 | 0.1 | 0.1 |
| 3 | 6.3E+05 | 69.0 | 18.7 | 4.9E+04 | 5.1 | 4.6 |
| 4 | 6.8E+05 | 67.3 | 19.3 | 5.3E+03 | 1.4 | 1.2 |
| 5 | 6.0E+05 | 65.6 | 17.9 | 1.0E+04 | 3.6 | 1.6 |
| 6 | 6.0E+05 | 76.9 | 18.6 | 4.9E+04 | 0.4 | 0.2 |
| 7 | 5.7E+05 | 77.3 | 24.8 | 1.0E+05 | 0.0 | 1.5 |
| 8 | 6.3E+05 | 76.0 | 17.2 | 9.9E+04 | 0.1 | 0.9 |
| 9 | 5.6E+05 | 64.2 | 14.6 | 1.4E+04 | 3.6 | 5.9 |
| E3 | 6.8E+05 | 63.5 | 18.2 | 7.1E+03 | 0.0 | 0.0 |

This study has identified the differential effects of SCF and Epo interactions on HSC expansion and differentiation into erythrocytes during a 21-day cell expansion experiment (FIGS. 12A-12C). Epo works synergistically to increase early expansion at a high level of SCF, but reduces expansion at low levels of SCF. At low SCF levels, Epo is more efficient at increasing CD235A expression; while at high SCF levels, Epo reduces erythrocytic differentiation.

In a second DOE study, a 3-level (SCF, Epo and cell density) full factorial experiment design was utilized to assess the interactions of cell seeding density to SCF and/or Epo (FIG. 13A). CD34$^+$ cells were obtained as described in FIG. 1, and E3 medium was supplemented with SCF and EPO with different cell densities shown in Table 11. It was demonstrated that significantly enhanced expansion (nearly 10-fold) can be achieved with lower Epo conditions (up to 3-fold), low cell density, and high SCF concentration (FIG. 13B). In addition, it was also demonstrated that erythrocytic differentiation can be improved using a higher cell seeding density and lower SCF concentration (FIG. 13C).

TABLE 11

Design of Experiment for E3 medium optimization

| RunOrder | Seed Density (#cell/mL) | EPO (IU/mL) | SCF (ng/mL) |
|---|---|---|---|
| 1 | 500000 | 5 | 1 |
| 2 | 50000 | 1 | 100 |
| 3 | 50000 | 5 | 100 |
| 4 | 50000 | 1 | 100 |
| 5 | 275000 | 3 | 50.5 |
| 6 | 275000 | 3 | 50.5 |
| 7 | 50000 | 5 | 1 |
| 8 | 500000 | 5 | 100 |
| 9 | 50000 | 1 | 1 |
| 10 | 500000 | 1 | 1 |
| 11 | 500000 | 1 | 100 |
| 12 | 500000 | 5 | 1 |
| 13 | 500000 | 1 | 100 |
| 14 | 50000 | 1 | 1 |
| 15 | 500000 | 1 | 100 |
| 16 | 50000 | 5 | 100 |
| 17 | 500000 | 1 | 1 |
| 18 | 50000 | 1 | 1 |
| 19 | 275000 | 3 | 50.5 |
| 20 | 500000 | 5 | 100 |
| 21 | 500000 | 5 | 100 |
| 22 | 50000 | 5 | 1 |
| 23 | 50000 | 5 | 1 |
| 24 | 50000 | 1 | 100 |
| 25 | 50000 | 5 | 100 |
| 26 | 500000 | 5 | 1 |
| 27 | 500000 | 1 | 1 |

6.9. Example 9: Method and Bioreactor for Generating Units of Erythrocytes

This Example provides a method of producing erythrocytes, and a bioreactor that enables the production of units of mature erythrocytes. In this particular example, the bioreactor enables the production of administrate units of erythrocytes using a five-step process. In the first step, hematopoietic cells, e.g., CD34$^+$ cells, are isolated. In the second step, the CD34$^+$ cells are expanded using an immunomodulatory compound, e.g., pomalidomide. In the third step, the CD34$^+$ cells are expanded in the bioreactor exemplified herein, in a co-culture with adherent placental stem cells, in conjunction with removal of lineage-committed cells. Fourth, remaining uncommitted hematopoietic cells are differentiated to erythrocytes. Finally, in the fifth step, erythrocytes are isolated and collected into administrate units.

Steps 1 and 2, the isolation and initial expansion of hematopoietic cells, are accomplished as described in Examples 3 and 4, above.

Steps 3 and 4 are accomplished using a bioreactor. The bioreactor comprises a hollow fiber chamber (1) needed with placental stem cells (2) and an element for gas provision to the medium (3). The bioreactor further comprises a coupled cell sorter/separator element (4) that allows for the continuous separation of committed hematopoietic cells, fully-differentiated erythrocytes, or both. The cell separation element can separate the cells from the hematopoietic cells using, e.g., magnetic cell separation or fluorescence-activated cell separation techniques.

To initiate cell culture, approximately 5×10$^7$ hematopoietic cells, e.g., CD34$^+$ hematopoietic cells, are inoculated into the bioreactor.

6.10. Example 10: Collection of Erythrocytes

This Example exemplifies several methods of the separation of erythrocytes from other lineage committed cells.

Method 1: Erythrocytes, e.g., erythrocytes collected from the cell separation element of the bioreactor exemplified herein, and hetastarch solution are mixed 3:1 (v:v) in a Baxter collection bag and placed in an upright position on a plasma extractor. Erythrocytes sediment after 50 to 70 minutes. Non-sedimented cells are forced out by the plasma extractor. Sedimented erythrocytes left in the bag can be further collected by centrifugation at 400×g for 10 minutes. After removing the supernatant, erythrocytes are resuspended in an appropriate amount of desired medium.

Method 2—Immunomagnetic separation: Glycophorin A+ cells, e.g., erythrocytes collected from the cell separation element of the bioreactor exemplified herein, are magnetically labeled with Glycophorin A (CD235a) MicroBeads (Miltenyi Biotech). The cell suspension is then loaded into a tube which is placed in the magnetic field of an EASY-SET® magnet. The magnetically labeled Glycophorin A+ cells are retained inside the tube, while the unlabeled cells are poured off the tube. After removal of the tube from the magnetic field, the magnetically retained Glycophorin A+ cells can be separated from the magnetic beads and resuspended in an appropriate amount of desired medium.

Method 3—Flow cytometry cell separation: Erythrocytes, e.g., erythrocytes collected from the cell separation element of the bioreactor exemplified herein, in 500 µL PBS/FBS with 1 µL Fc Block (1/500), 150 µL of the cell suspension is added to each well of a 96 well V-bottom dish. 50 µL 1° Ab Master Mix (the mix is a 1/25 dilution of each primary Ab in PBS/FBS) is added to the cells. One well is included with a combination of isotype controls for setting voltage, as well as one well for each of the primary Ab as single positive controls for setting compensation. The cells are incubated 60 min at 4° C., then centrifuged at 1500 RPM for two minutes. The supernatant is discarded. The wells are washed with 200 µL PBS/FBS to each well, and mixed by pipetting up and down. The cells are then immediately spun at 1500 RPM×2 min; the supernatant is discarded. 150 µL of secondary Ab (i.e. Streptavidin-TC) Master Mix is added, and incubated 30 min at 4° C., followed by centrifugation at 1500 RPM for 5 minutes. The pellet is resuspended in 200-500 µL of PBS/FBS and transferred to 5 mL flow tubes. Cells are then separated using a flow cytometer.

Method 4: Medium comprising erythrocytes, in continuous flow between the cell culture element and cell separation element, is deoxygenated by reducing or turning off the supply of oxygen from the gas provision element, and turning on a magnet in the cell separation element. Medium is passed through the cell separation element for a sufficient time for the magnetic field of the magnet to collect erythrocytes to a surface in the cell separation element. Once a predetermined number of erythrocytes are collected, or collection has proceeded for a predetermined amount of time, the medium is reoxygenated, releasing the erythrocytes from the surface.

Method 5: Sedimentation based erythrocyte enrichment. Erythrocyte enrichment can be performed by centrifugation at 3000 rpm for 15 min with break off. Leukocytes (top white layer), immature erythrocytes (middle pink layer), and erythrocytes (bottom red layer) can be separated. Erythrocytes are then collected from the bottom and resuspended in an appropriate amount of desired medium.

6.11. Collection of Erythrocytes

This Example demonstrates the collection of erythrocytes using flow cytometry,

Erythrocyte enrichment was performed by FACSAria sorting to select erythrocytes by cell size using light scatter (forward and side scatter, FIG. 14 and Table 12) or enucleation using DRAQ5 labeling (linear APC channel fluorescence, FIG. 15 and Table 13).

After cell sorting by FACSAria, cells gated by P1, P2 and P3 were assessed for proportion of HbA+ enucleation and CD235A+ by flow cytometry. P1 cells showing smallest cell size exhibited highest percent HbA+, percent enucleation and percent CD235A+, and therefore were mostly erythrocytes.

TABLE 12

Characterization of sorted erythrocyte populations by cell size

| | Samples | Living cells | P1 | P2 | P3 | % HbA+ | % Enucleation | % CD235A+ |
|---|---|---|---|---|---|---|---|---|
| Presort | | 63.50% | 26.18% | 34.34% | 13.39% | 28.2 | 22.2 | 69.8 |
| Sorted | P1 | 50.34% | 62.04% | — | — | 30.3 | 61.5 | 92.1 |
| | P2 | 49.66% | — | 53.31% | — | 14.31 | 33.7 | 76.4 |
| | P3 | 54.01% | — | — | 30.24% | 18.12 | 2.64 | 74.84 |

In Table 12, cells were stained by cell permeable DNA-interactive agent DRAQ5 (Cell Signaling, Catalog No. #4084) followed by cell sorting using FACSAria, cells gated by Q1 and Q2 were assessed for proportion of HbA+, enucleation and CD235A+ by flow cytometry. Q1 cells that were negative for DRAQ staining, exhibited higher percent HbA+, percent enucleation and percent CD235A+ compared with Q2 cells, and therefore were mostly erythrocytes.

TABLE 13

Characterization of sorted erythrocyte populations by DRAQ5 staining

| | | Living cells | APC+ | APC− | % HbA+ | % Enucleation | % CD235A+ |
|---|---|---|---|---|---|---|---|
| Presort | | 64.51% | 13.76% | 47.83% | 28.2 | 22.2 | 69.8 |
| Sorted | Q1 DRAQ5 Negative | 49.69% | | 82.12% | 24.93 | 60.7 | 91.8 |
| | Q2 DRAQ5 Positive | 30.20% | 39.72% | | 18.96 | 15.4 | 65.7 |

As depicted in Table 13, cells were stained by cell permeable DMA-interactive agent DRAQ5. After cell sorting by FACSAria, cells gated by QP1, P2 and QP3 were assessed for proportion of HbA$^+$ enucleation and CD235A$^+$ by flow cytometry. QP1 cells that were negative for DRAQ staining, showing smallest cell size exhibited the highest percent HbA$^+$, percent enucleation and percent CD235A$^+$ compared with Q2 cells, and therefore were predominantly erythrocytes.

6.12. Example 11: Bioreactor for Producing Erythrocytes

This Example describes a bioreactor design that allows for improved production of erythrocytes from hematopoietic cells. The bioreactor comprises a culturing element that comprises hollow fibers in which hematopoietic cells are cultured. Hematopoietic cells, e.g., hematopoietic progenitor cells, are supplied in a bag at 5×10$^5$ cells/dose, where one dose yields one unit of blood. The cells are expanded in the presence of IMDM medium containing 50 ng/mL SCF, 3 units/ml. Epo, and 50 ng/mL IGF-1 added through a first port. Gas provision (5% CO2 in air) occurs through a second port. The medium in which the hematopoietic cells are cultured is supplemented with pomalidomide at 2.7 µg/mL. During culturing, gas, medium metabolites and medium pH in the culturing element is monitored continuously, and are replenished or exchanged using a programmable control device as necessary. pH of the medium in the culturing element is maintained at approximately 7 and the culture temperature is maintained at about 37° C. Lineage-committed cells (i.e., differentiated ceils) are continuously separated and recovered from the culture medium using a cell separation element. The bioreactor is equipped with an independent power supply to enable operation at a remote site, e.g., a site separate from a site at which hematopoietic ceils are initially obtained.

The present disclosure, including devices, compositions and methods, is not to be limited in scope by the specific embodiments described herein. Indeed, various modifications in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirely for all purposes.

The citation of any publication is for its disclosure prior to the filing date and should not be construed as art admission that the present disclosure is not entitled to antedate such publication by virtue of prior invention.

What is claimed is:

1. A method of producing erythrocytes, comprising:
    a) expanding a first population of hematopoietic cells in a first medium in the absence of feeder cells to obtain an expanded population of hematopoietic cells, wherein the first population of hematopoietic cells has an initial cell density of 5×10$^4$ cells/mL or less and the first medium comprises Epo at a concentration of 1 IU/mL or less and SCF at a concentration of 100 ng/mL or more;
    b) differentiating a plurality of hematopoietic cells within said expanded population of hematopoietic cells into erythrocytes by contacting the expanded population of hematopoietic cells with a second medium, wherein the expanded population of hematopoietic cells has an initial cell density greater than 2.75×10$^5$ cells/mL and the second medium comprises Epo at a concentration of 3 IU/mL or greater and SCF at a concentration of 50 ng/mL or less; and
    c) isolating said erythrocytes from said second medium, wherein said SCF and Ep are not comprised within an undefined component of said first or said second medium.

2. The method of claim 1, wherein the first medium further comprises pomalidomide.

3. The method of claim 1, wherein the first medium does not comprise one or more of Flt-3L, IL-11, thrombopoietin (Tpo), homeobox-B4 (HoxB4), or methylcellulose.

4. The method of claim 1, wherein the second medium does not comprise one or more of Flt-3L, IL-11, thrombopoietin (Tpo), homeobox-B4 (HoxB4), or methylcellulose.

5. The method of claim 1, wherein the first population of hematopoietic cells has an initial cell density between 2×10$^4$ and 5×10$^4$ cells/mL.

6. The method of claim 1, wherein the first population of hematopoietic cells comprises hematopoietic cells from a plurality of individuals.

7. The method of claim 1, wherein the first population of hematopoietic cells comprises hematopoietic cells from placenta.

8. The method of claim 1, wherein the first population of hematopoietic cells comprise cells from two or more tissue sources.

9. The method of claim 1, wherein the first medium further comprises IGF-1 at a concentration of about 1 to about 1000 ng/mL.

10. The method of claim 1, wherein the first medium further comprises lipids at a concentration of about 1 to about 1000 µg/mL.

* * * * *